United States Patent

Schumacher

[11] Patent Number: 5,770,709
[45] Date of Patent: Jun. 23, 1998

[54] FIBER REACTIVE AZO DYES CONTAINING A 2-QUINOLONE DIAZO COMPONENT RADICAL

[75] Inventor: Christian Schumacher, Kelkheim, Germany

[73] Assignee: DyStar Textilfarben GmbH & Co Deutschland KG, Frankfurt am Main, Germany

[21] Appl. No.: 925,540

[22] Filed: Sep. 8, 1997

[30] Foreign Application Priority Data

Sep. 9, 1996 [DE] Germany .................. 196 36 483.3

[51] Int. Cl.⁶ .................. C09B 62/006; C09B 62/026
[52] U.S. Cl. .................. 534/633; 534/634; 534/635; 534/642
[58] Field of Search .................. 534/633, 634, 534/635

[56] References Cited

U.S. PATENT DOCUMENTS 5,539,088   7/1996   Schumacher et al. .................. 534/633

*Primary Examiner*—Fiona T. Powers
*Attorney, Agent, or Firm*—Connolly & Hutz

[57] ABSTRACT

Water-soluble azo compounds, processes for their preparation and their use as dyestuffs.

Water-soluble azo compounds are described which have fiber-reactive properties and are suitable as dyestuffs for dyeing material, in particular fiber material, containing hydroxy and/or carboxamide groups, such as, for example, cellulosic fiber materials, such as those of cotton, wool or nylon, and which have, as the radical of a diazo component, a radical of the formula

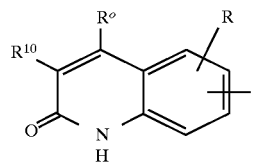

in which R is hydrogen, alkyl having 1 to 4 carbon atoms, alkoxy having 1 to 4 carbon atoms, halogen or sulfo, $R^o$ is hydrogen, alkyl having 1 to 4 carbon atoms, halogen, carboxy, aminocarbonyl, alkoxycarbonyl having 2 to 5 carbon atoms, sulfo or phenyl and $R^{10}$ is hydrogen, alkyl having 1 to 4 carbon atoms or halogen, and which contain a fiber-reactive radical bonded to the coupling component via an amino group.

20 Claims, No Drawings

FIBER REACTIVE AZO DYES CONTAINING A 2-QUINOLONE DIAZO COMPONENT RADICAL

The invention relates to the technical field of fiber-reactive dyestuffs.

Fiber-reactive azo compounds with dyestuff properties which contain a heterocyclic diazo component are already known from U.S. Pat. No. 5,539,088. The object of the present invention was to discover novel fiber-reactive dyestuffs which meet the increased requirements of the industry and of quality and produce dyeings with brilliant color shades and very good fastnesses during use at a high degree of fixing.

Novel azo compounds with improved fiber-reactive dyestuff properties have been found with the present invention. The novel azo compounds correspond to the formula (1)

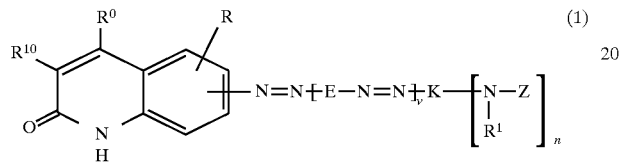

in which:

R° is hydrogen, alkyl having 1 to 4 carbon atoms, such as methyl and ethyl, halogen, such as chlorine, bromine and fluorine, sulfo, carboxy, aminocarbonyl, alkoxycarbonyl having 2 to 5 carbon atoms, such as methoxycarbonyl and ethoxycarbonyl, or phenyl, preferably hydrogen or alkyl having 1 to 4 carbon atoms;

$R^{10}$ is hydrogen, alkyl having 1 to 4 carbon atoms, such as ethyl and methyl, or halogen, such as chlorine, bromine or fluorine, preferably hydrogen;

$R^1$ is hydrogen, alkyl having 1 to 4 carbon atoms, such as ethyl and, in particular, methyl, alkoxy having 1 to 4 carbon atoms, such as ethoxy and, in particular, methoxy, halogen, such as chlorine or bromine, or sulfo, preferably hydrogen;

$R^1$ is hydrogen, alkyl having 1 to 4 carbon atoms, such as ethyl and, in particular, methyl, or alkyl having 1 to 4 carbon atoms, such as, in particular, ethyl, which is substituted by hydroxy, cyano, alkoxy having 1 to 4 carbon atoms, such as ethoxy and methoxy, carboxy, sulfo, sulfato or phosphato, or is phenyl or naphthyl, both of which can be substituted by 1, 2 or 3 substituents from the group consisting of halogen, such as chlorine and bromine, hydroxy, cyano, alkoxy having 1 to 4 carbon atoms, such as ethoxy and, in particular, methoxy, alkyl having 1 to 4 carbon atoms, such as ethyl and, in particular, methyl, alkoxycarbonyl having 2 to 5 carbon atoms, such as ethoxycarbonyl and methoxycarbonyl, carboxy, sulfamoyl, sulfo and alkylsulfonyl with an alkyl radical having 1 to 4 carbon atoms, such as methylsulfonyl and ethylsulfonyl, and of these substituents preferably alkoxy having 1 to 4 carbon atoms, alkyl having 1 to 4 carbon atoms, carboxy and sulfo;

E is the bivalent radical, which is free from the amino group, of a compound from the aniline or naphthylamine series which is capable of coupling and can be diazotized;

v represents the number zero, 1 or 2, preferably zero or 1, and particularly preferably zero;

K is the bivalent radical, which is free from the amino group, of a coupling component of the aniline or naphthylamine series or the bivalent radical of a coupling component of the heterocyclic series;

n is the number 1 or 2, preferably 1;

Z is the fiber-reactive radical of a fiber-reactive grouping or group, where, if n is greater than 1, the radicals —N($R^1$)—Z can have different meanings to one another; and the compounds of the formula (1) have at least one, preferably several, such as two, three, four or five, sulfo groups.

Z is preferably a radical of the formula (3a), (3b) or (3c)

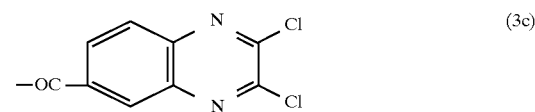

in which:

$X^1$ is halogen, such as chlorine and fluorine, or cyanoamino or a group of the formula (4)

in which $R^2$ is hydrogen, alkyl having 1 to 4 carbon atoms, such as ethyl and, in particular, methyl, or alkyl having 1 to 4 carbon atoms, such as, in particular, ethyl, which is substituted by hydroxy, cyano, alkoxy having 1 to 4 carbon atoms, such as ethoxy and methoxy, carboxy, sulfo, sulfato or phosphate, or is phenyl or naphthyl, both of which can be substituted by 1, 2 or 3 substituents from the group consisting of halogen, such as chlorine and bromine, hydroxy, cyano, alkoxy having 1 to 4 carbon atoms, such as ethoxy and, in particular, methoxy, alkyl having 1 to 4 carbon atoms, such as ethyl and, in particular, methyl, alkoxycarbonyl having 2 to 5 carbon atoms, such as ethoxycarbonyl and methoxycarbonyl, carboxy, sulfamoyl, sulfo and alkylsulfonyl with an alkyl radical having 1 to 4 carbon atoms, such as methylsulfonyl and ethylsulfonyl, and of these substituents preferably alkoxy having 1 to 4 carbon atoms, alkyl having 1 to 4 carbon atoms, carboxy and sulfo, W is alkylene having 2 to 4 carbon atoms, preferably 2 or 3 carbon atoms, such as 1,2-ethylene and 1,3-propylene, or is alkylene having 3 to 6 carbon atoms, preferably 4 carbon atoms, which is interrupted by 1 or 2 hetero groups from the group consisting of the formulae —O—, —NH—, —$SO_2$—, —CO— and —N($R^A$)— (where $R^A$ is hydrogen or alkyl having 1 to 4 carbon atoms, such as methyl and ethyl, or is phenyl or naphthyl which are optionally substituted by 1 to 3 substituents from the group consisting of sulfo, carboxy, alkoxy having 1 to 4 carbon atoms, such as methoxy, alkyl having 1 to 4 carbon atoms, such as methyl, halogen, such as chlorine, cyano and nitro), such as, for example, groups of the formulae —(CH$_2$)$_2$—O—(CH$_2$)$_2$— and —(CH$_2$)$_2$—NH—(CH$_2$)$_2$—, or W is phenylene or naphthylene, both of which can be substituted by 1, 2 or 3 substituents from the group consisting of halogen, such as chlorine and bromine, hydroxy, cyano, nitro, alkoxy having 1 to 4 carbon atoms, such as ethoxy and, in particular, methoxy, alkyl having 1 to 4 carbon atoms, such as ethyl and, in particular, methyl, alkoxycarbonyl having 2 to 5 carbon atoms, such as ethoxycarbonyl and methoxycarbonyl, carboxy, sulfamoyl and sulfo, and of these substituents preferably alkoxy having 1 to 4 carbon atoms, alkyl having 1 to 4 carbon atoms, carboxy and sulfo, or is phenylenealkylene or alkylenephenylene with an alkylene radical having in each case 1 to 4 carbon atoms, such as, in particular, ethylene, and A is vinyl, or is ethyl which is substituted in the β-position by a substituent which can be split off by means of alkali to form the vinyl group;

$Y^1$ is chlorine or a group of the formula (5)

(5)

in which
  $R^3$ is hydrogen, alkyl having 1 to 4 carbon atoms, such as ethyl and methyl, or alkyl having 1 to 4 carbon atoms, such as, in particular, ethyl, which is substituted by halogen, such as chlorine and bromine, hydroxy, cyano, alkoxy having 1 to 4 carbon atoms, such as ethoxy and methoxy, alkoxycarbonyl having 2 to 5 carbon atoms, such as ethoxycarbonyl and methoxycarbonyl, carboxy, sulfo, sulfato or phosphato, or is a group of the formula —W—SO$_2$—A where W and A have one of the abovementioned meanings, and
  $R^4$ is hydrogen, alkyl having 1 to 4 carbon atoms, such as ethyl and methyl, or alkyl having 1 to 4 carbon atoms, such as, in particular, ethyl, which is substituted by halogen, such as chlorine and bromine, hydroxy, cyano, alkoxy having 1 to 4 carbon atoms, such as ethoxy and methoxy, alkoxycarbonyl having 2 to 5 carbon atoms, such as ethoxycarbonyl and methoxycarbonyl, carboxy, sulfo, sulfato or phosphate, or is cycloalkyl having 5 to 8 carbon atoms, such as cyclohexyl, or a group of the formula —W—SO$_2$—A where W and A have one of the abovementioned meanings, or is phenyl or naphthyl, both of which can be substituted by 1, 2 or 3 substituents from the group consisting of halogen, such as chlorine and bromine, hydroxy, cyano, alkoxy having 1 to 4 carbon atoms, such as ethoxy and, in particular, methoxy, alkyl having 1 to 4 carbon atoms, such as ethyl and, in particular, methyl, alkoxycarbonyl having 2 to 5 carbon atoms, such as ethoxycarbonyl and methoxycarbonyl, carboxy, sulfamoyl, sulfo and alkylsulfonyl with an alkyl radical having 1 to 4 carbon atoms, such as ethylsulfonyl and methylsulfonyl, or
  $R^3$ and $R^4$ together are an alkylene radical having 3 to 6 carbon atoms or an alkylene radical having 3 to 6 carbon atoms which is interrupted by a group —NH—, —O—, —CO—, —S—, —SO$_2$— or —N(R$^5$)— (in which R$^5$ is alkyl having 1 to 4 carbon atoms, such as ethyl, which is substituted by sulfo or sulfato), which, together with the N atom, form a heterocyclic radical, such as the pyrrolidino, morpholino, piperidino or piperazino radical, or $Y^1$ is a group of the formula (3A)

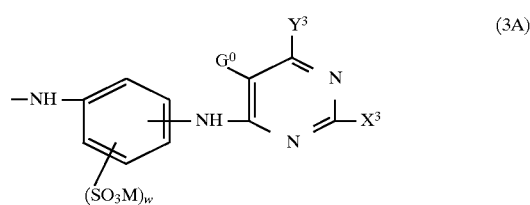

(3A)

in which
  M is a hydrogen atom or an alkali metal, such as sodium, potassium or lithium, or another salt-forming metal,
  w is the number zero, 1 or 2 (where, if w is zero, this group is hydrogen),
  $G^o$ is hydrogen or halogen, such as chlorine, or cyano,
  $X^3$ is hydrogen, halogen, such as chlorine or fluorine, or alkylsulfonyl having 1 to 4 carbon atoms, such as methylsulfonyl or ethylsulfonyl, preferably fluorine, and
  $Y^3$ is halogen, such as chlorine or fluorine, or methyl, preferably fluorine;
  G is hydrogen or halogen, such as chlorine, or cyano;
  $X^2$ is hydrogen, halogen, such as chlorine or fluorine, or alkylsulfonyl having 1 to 4 carbon atoms, such as methylsulfonyl or ethylsulfonyl, preferably fluorine, and
  $Y^2$ is hydrogen, halogen, such as chlorine or fluorine, or methyl, preferably fluorine, where at least one of the radicals $X^2$ and $Y^2$ is halogen or alkylsulfonyl.

Both in the above formulae and in the following formulae, the individual formula members, both of a different and of the same meaning within a formula, can have meanings which are identical to one another or different from one another within the scope of their meaning.

Substituents which can be eliminated under alkaline conditions and are in the β-position of the ethyl group of A are, for example, halogen atoms, such as bromine and chlorine, ester groups of organic carboxylic and sulfonic acids, such as of alkylcarboxylic acids, optionally substituted benzenecarboxylic acids and optionally substituted benzenesulfonic acids, such as the groups alkanoyloxy having 2 to 5 carbon atoms, and of these in particular acetyloxy, benzoyloxy, sulfobenzoyloxy, phenylsulfonyloxy and toluylsulfonyloxy, and furthermore acidic ester groups of inorganic acids, such as of phosphoric acid, sulfuric acid and thiosulfuric acid (phosphato, sulfato and thiosulfato groups), and also dialkylamino groups with alkyl groups having in each case 1 to 4 carbon atoms, such as dimethylamino and diethylamino. A is preferably β-chloroethyl or vinyl, and particularly preferably β-sulfatoethyl.

The groups "sulfo", "carboxy", "thiosulfato", "phosphato" and "sulfato" include both the acid form thereof and the salt form thereof. Accordingly, sulfo groups are groups corresponding to the formula —SO$_3$M, carboxy groups are groups corresponding to the formula —COOM, thiosulfato groups are groups corresponding to the formula —S—SO$_3$M, phosphato groups are groups corresponding to the formula —OPO$_3$M$_2$ and sulfato groups are groups corresponding to the formula —OSO$_3$M, in which M has the abovementioned meaning.

$R^1$ is preferably hydrogen, methyl or ethyl, in particular hydrogen, and $R^2$ is preferably hydrogen, methyl, ethyl or phenyl.

$X^1$ is preferably chlorine, fluorine or cyanoamino.

$Y^1$ is preferably a radical of the formula (5), in particular phenylamino, which can be substituted by 1, 2 or 3, preferably 1 or 2, substituents from the group consisting of halogen, such as chlorine and bromine, hydroxy, cyano, ethoxy, methoxy, methyl, ethyl, carboxy and sulfo, preferably sulfo, or naphthylamino, preferably naphth-2-ylamino, which is substituted by 1, 2 or 3 sulfo groups, and in particular preferably morpholino, and furthermore a group of the formula (4a) or (4b) or (4c)

in which

W and A have one of the abovementioned meanings and $R^6$ is hydrogen, alkyl having 1 to 4 carbon atoms, such as ethyl and, in particular, methyl, or alkyl having 1 to 4 carbon atoms, such as, in particular, ethyl, which is substituted by hydroxy, cyano, alkoxy having 1 to 4 carbon atoms, such ethoxy and methoxy, carboxy, sulfo, sulfato or phosphato, or is phenyl or naphthyl, both of which can be substituted by 1, 2 or 3 substituents from the group consisting of halogen, such as chlorine and bromine, hydroxy, cyano, alkoxy having 1 to 4 carbon atoms, such as ethoxy and, in particular, methoxy, alkyl having 1 to 4 carbon atoms, such as ethyl and, in particular, methyl, alkoxycarbonyl having 2 to 5 carbon atoms, such as ethoxycarbonyl and methoxycarbonyl, carboxy, sulfamoyl, sulfo and alkylsulfonyl with an alkyl radical having 1 to 4 carbon atoms, such as methylsulfonyl and ethylsulfonyl, and of these preferably alkoxy having 1 to 4 carbon atoms, alkyl having 1 to 4 carbon atoms, carboxy and sulfo, and $W^0$ is alkylene having 3 to 6 C atoms, preferably 4 C atoms, which is interrupted by 1 or 2 hetero groups from the group consisting of the formulae —O—, —NH—, —SO$_2$— and —CO—, such as, for example, a group of the formula —(CH$_2$)$_2$—O—(CH$_2$)$_2$— or —(CH$_2$)$_2$—NH—(CH$_2$)$_2$—.

Of the radicals of the formula (3b), the difluoro-chloropyrimidino, difluoropyrimidino, trichloro-pyrimidino, methylsulfonyl-chloro-pyrimidino and methylfluoro-chloro-pyrimidino radicals are particularly preferred.

Radicals of the formula (1a)

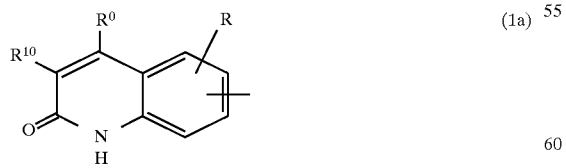

in the compounds of the formula (1) are, for example, 4-methyl-quinolin-2-ol-6-yl, 4-ethyl-quinolin-2-ol-6-yl, 4-methyl-quinolin-2-ol-5-yl, 4-ethyl-quinolin-2-ol-5-yl, 4-carboxy-quinolin-2-ol-6-yl, 7-methoxy-4-methyl-quinolin-2-ol-6-yl, 7-sulfo-4-methyl-quinolin-2-ol-6-yl, 8-methoxy-4-methyl-quinolin-2-ol-6-yl, 5-bromo-4-methyl-quinolin- 2-ol-6-yl, 3-bromo-4methyl-quinolin-2-ol-6-yl, 5-chloro-4-methyl-quinolin-2-ol-6-yl, 3-chloro-4-methyl-quinolin-2-ol-6-yl, 8-chloro-4-methyl-quinolin-2-ol-6-yl, 8-methoxy-quinolin-2-ol-6-yl, 8-chloro-quinolin-2-ol-6-yl, 4-aminocarbonyl-quinolin-2-ol-6-yl and 4ethoxycarbonyl-quinolin-2-ol-6-yl.

Aromatic radicals E of a compound of the formula H—E—NH$_2$ which is capable of coupling and can be diazotized are, for example, those of the formulae (6a), (6b) and (6c)

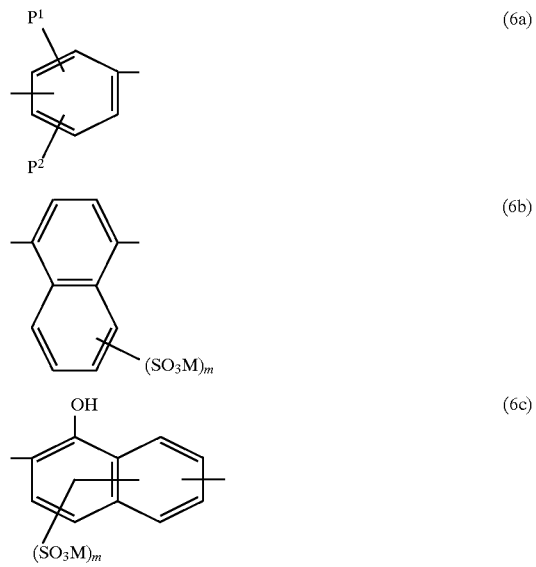

in which

M has the abovementioned meaning, m is the number zero, 1 or 2 (where, if m is zero, this group is hydrogen), $P^1$ is hydrogen, alkyl having 1 to 4 carbon atoms, such as ethyl, methyl, alkoxy having 1 to 4 carbon atoms, such as ethoxy and methoxy, cyano, sulfo, carboxy, hydroxy, fluorine, chlorine, bromine or trifluoromethyl, and $P^2$ is hydrogen, alkyl having 1 to 4 carbon atoms, such as methyl or ethyl, alkoxy having 1 to 4 carbon atoms, such as methoxy and ethoxy, chlorine, alkanoylamino having 2 to 5 carbon atoms, such as acetylamino and propionylamino, amino, benzoylamino, ureido, phenylureido, alkylureido having 1 to 4 carbon atoms in the alkyl radical, phenylsulfonyl or alkylsulfonyl having 1 to 4 carbon atoms.

Radicals —K—N($R^1$)—Z of coupling components of the formula H—K—N($R^1$)—Z (or radicals of the formula H—K—N($R^1$)H derived therefrom, into which the fiber-reactive radical Z must subsequently be introduced) are, for example, radicals of the formulae (7a) to (7f)

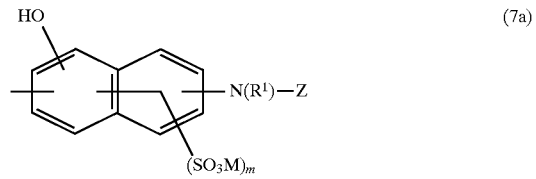

-continued (7b)

[Structure: naphthalene with —N(R¹)—Z and (SO₃M)ₘ substituents]

(7c)

[Structure: benzene ring with P¹, P², and —N(R¹)—Z substituents]

(7d)

[Structure with HO—, P³, N—T—N(R¹)—Z, P⁴, P⁵, N]

(7e)

[Pyridinone structure with P⁶, P⁷, HO—, N, O, B—N(R¹)—Z]

(7f)

[Structure: HO— naphthalene —NH—CO—V—N(R¹)—Z with (SO₃M)ₘ]

in which:

P¹, P², M, m, R¹ and Z have the abovementioned, particularly preferred, meanings;

in formula (7a), the free bond which leads to the azo group is bonded in the ortho-position to the hydroxy group on the aromatic nucleus;

P³ is hydrogen, alkyl having 1 to 4 carbon atoms, such as ethyl and, in particular, methyl, alkoxy having 1 to 4 carbon atoms, such as ethoxy and, in particular, methoxy, chlorine, bromine, fluorine, sulfo, carboxy or trifluoromethyl;

P⁴ is hydrogen, alkyl having 1 to 4 carbon atoms, such as ethyl and, in particular, methyl, alkoxy having 1 to 4 carbon atoms, such as ethoxy and, in particular, methoxy, chlorine or sulfo;

P⁵ is hydrogen, alkyl having 1 to 4 carbon atoms, such as methyl, cyano, carboxy, carbalkoxy having 2 to 5 carbon atoms, such as carbomethoxy and carbethoxy, carbamoyl or phenyl, preferably methyl, carboxy, methoxycarbonyl, ethoxycarbonyl or phenyl, and in particular methyl or carboxy;

T is a benzene or naphthalene ring, preferably a benzene ring;

P⁶ is hydrogen or alkyl having 1 to 4 carbon atoms, such as methyl, or alkyl having 1 to 4 carbon atoms which is substituted by alkoxy having 1 to 4 carbon atoms, such as methoxy, or by cyano, or phenyl, preferably alkyl having 1 to 4 carbon atoms or phenyl;

P⁷ is hydrogen, chlorine, bromine, sulfo, carbamoyl, methylsulfonyl, phenylsulfonyl, cyano or sulfoalkyl having 1 to 4 carbon atoms, preferably hydrogen, sulfo, sulfoalkyl with an alkyl radical having 1 to 4 carbon atoms, such as sulfomethyl, cyano or carbamoyl; and V is phenylene, preferably meta- or para-phenylene, which can be substituted by a sulfo group.

Groups corresponding to the formulae (4) and (4a) are, for example: N-[γ-(β'-chloroethylsulfonyl)propyl]amino, N-[γ-(β'-sulfatoethylsulfonyl)-propyl]amino, N-[γ-(vinylsulfonyl)propyl]amino, N-[β-(β'-chloroethylsulfonyl)ethyl]amino, N-[β-(β'-sulfatoethylsulfonyl)ethyl]amino, N-[β-(vinyl-sulfonyl)ethyl]amino, N-methyl-N-[β-(β'-chloroethylsulfonyl)ethyl]amino, N-ethyl-N-[β-(β'-chloroethylsulfonyl)propyl]amino, N-n-propyl-N-[β-(β'-chloro-ethylsulfonyl)ethyl]amino, N-n-butyl-N-[β-(β'-chloroethylsulfonyl)ethyl]]amino, N-carboxymethyl-N-[β-(β'-bromoethylsulfonyl)ethyl]amino, N-sulfatomethyl-N-[β-(β'-chloroethylsulfonyl)ethyl]amino, N-(β-carboxyethyl)-N-[β'-(β''-chloroethylsulfonyl)ethyl]amino, N-(β-sulfatoethyl)-N-[β'-(β''-chloroethylsulfonyl)ethyl]amino, N-(β-ethoxyethyl)-N-[β'-(β''-chloro-ethylsulfonyl)ethyl]amino, N-phenyl-N-[β-(β'-chloroethylsulfonyl)ethyl]amino, N-(4-chlorophenyl)-N-[β-(β'-chloroethylsulfonyl)ethyl]amino, N-(2-methylphenyl)-N-[β-(β'-chloroethylsulfonyl)ethyl]amino, N-(4-methoxyphenyl)-N-[β-(β'-chloroethylsulfonyl)ethyl]amino, N-(3-sulfophenyl)-N-[β-(β'-chloroethylsulfonyl)ethyl]amino, N-(4-sulfophenyl)-N-[β-(β'-chloroethylsulfonyl)ethyl]amino, N-(β-cyanoethyl)-N-[β'-(β''-chloroethylsulfonyl)ethyl]amino, N-phenyl-N-(β-vinylsulfonylethyl)amino, N-(4-chlorophenyl)-N-(β-vinylsulfonylethyl)amino, N-(2-methylphenyl)-N-(β-vinylsulfonylethyl)amino, N-(4-methoxyphenyl)-N-(β-vinylsulfonyl-ethyl)amino, N-(3-sulfophenyl)-N-(β-vinylsulfonylethyl)amino, N-(4-sulfophenyl)-N-(β-vinylsulfonylethyl)amino, N-phenyl-N-[β-(β'-sulfatoethylsulfonyl)ethyl]amino, N-(4-chlorophenyl)-N-[β-(β'-sulfatoethylsulfonyl)ethyl]amino, N-(2-methylphenyl)-N-[β-(β'-sulfatoethylsulfonyl)ethyl]amino, N-(4-methoxyphenyl)-N-[β(β'-sulfatoethylsulfonyl)ethyl]amino, N-(3-sulfophenyl)-N-[β-(β'-sulfatoethylsulfonyl)ethyl]amino, N-(4-sulfophenyl)-N-[β-(β'-sulfatoethylsulfonyl)ethyl]amino, N-methyl-N-[γ-(β'-chloroethylsulfonyl)propyl]amino, N-ethyl-N-[γ-(β'-chloroethylsulfonyl)propyl]amino, N-n-propyl-N-[γ-(β'-chloroethylsulfonyl)propyl]amino, N-n-butyl-N-[γ-(β'-chloroethylsulfonyl)propyl]amino, N-carboxymethyl-N-[γ-(β'-bromoethylsulfonyl)propyl]amino, N-sulfatomethyl-N-[γ-(β'-chloroethylsulfonyl)-propyl]amino, N-(β-carboxyethyl)-N-[γ'-(β''-chloroethylsulfonyl)propyl]amino, N-(β-sulfatoethyl)-N-[γ'-(β''-chloroethylsulfonyl)propyl]amino, N-(β-sulfatoethyl)-N-[δ'-(β''-chloroethylsulfonyl)butyl]amino, N-(β-ethoxyethyl)-N-[δ'-(β''-chloroethylsulfonyl)butyl]amino, N-(β-ethoxyethyl)-N-[γ'-(β''-chloroethylsulfonyl)propyl]amino, N-phenyl-N-[γ-(β'-chloroethylsulfonyl)propyl]amino, N-(4-chlorophenyl)-N-[γ-(β'-chloroethylsulfonyl)propyl]amino, N-(2-methylphenyl)-N-[γ-(β'-chloroethylsulfonyl)propyl]amino, N-(4-methoxyphenyl)-N-[γ-(β'-chloroethylsulfonyl)propyl]amino, N-(3-sulfophenyl)-N-[γ-(β'-chloroethylsulfonyl)propyl]amino, N-(4-sulfophenyl)-N-[γ-(β'-chloroethylsulfonyl)propyl]amino, N-(β-cyanoethyl)-N-[γ'-(β''chloro-ethylsulfonyl)propyl]amino, N-phenyl-N-(γ-vinylsulfonylpropyl)amino, N-(4-chlorophenyl)-N-(γ-vinylsulfonylpropyl)amino, N-(2-methylphenyl)-N-(γ-vinylsulfonylpropyl)amino, N-(4-methoxyphenyl)-N-(γ-vinylsulfonylpropyl)amino, N-(3-sulfophenyl)-N-(γ- vinylsulfonylpropyl)-amino, N-(4-sulfophenyl)-N-(γ-vinylsulfonylpropyl)amino, N-phenyl-N-[γ-(β'-sulfatoethylsulfonyl)propyl]amino, N-(4-chlorophenyl)-N-[γ-(β'-sulfatoethylsulfonyl)propyl]amino, N-(2-methylphenyl)-N-[γ-(β'-sulfatoethylsulfonyl)propyl]amino, N-(4-methoxyphenyl)-N-[γ-(β'-sulfatoethylsulfonyl)propyl]amino, N-(3-sulfophenyl)-N-[γ-(β'-sulfatoethylsulfonyl)propyl]amino, N-(4-sulfophenyl)-N-[γ-(β'-sulfatoethylsulfonyl)propyl]amino, N-phenyl-N-[α-carboxy-γ-(β'-chloroethylsulfonyl)propyl]amino, N-phenyl-N-[α-ethoxycarbonyl-γ-(β'-chloroethylsulfonyl)propyl]amino, N-phenyl-N-[α-methoxycarbonyl-γ-(β'-chloroethylsulfonyl)propyl]amino, N-phenyl-N-[β-methyl-γ-(β'-chloroethylsulfonyl)propyl]amino, N-phenyl-N-[(β-ethyl-γ-(β'-chloroethylsulfonyl)-propyl]amino, N-phenyl-N-[δ-(β'-chloroethylsulfonyl)butyl]amino, N-phenyl-N-[ε-(β'-chloroethylsulfonyl)pentyl]amino and N-phenyl-N-[β-(β'-chloroethylsulfonyl)hexyl]amino, bis-N,N-[γ-(β'-chloroethylsulfonyl)propyl]amino, bis-N,N-[γ-(β'-sulfatoethylsulfonyl)propyl]amino, bis-N,N-[γ-(vinylsulfonyl)-propyl]amino, bis-N,N-[β-(β'-chloroethylsulfonyl)ethyl]amino, bis-N,N-[β(β'-sulfatoethylsulfonyl)ethyl]amino, bis-N,N-[β-(vinylsulfonyl)ethyl]amino, 4-(β-sulfatoethylsulfonyl)phenylamino, 3-(β-sulfatoethylsulfonyl)phenylamino, 2-methoxy-5-(β-sulfatoethylsulfonyl)phenylamino, 2,5-dimethoxy-4-(β-sulfatoethylsulfonyl)phenylamino, 2-methoxy-5-methyl-4-(β-sulfatoethylsulfonyl)phenylamino, 2-sulfo-4-(β-sulfatoethylsulfonyl)-phenylamino, 2-hydroxy-5-(β-sulfatoethylsulfonyl)phenylamino, 2-bromo-5-(β-sulfatoethylsulfonyl)phenylamino, 4-[β-(β'-sulfatoethylsulfonyl)ethyl]-phenylamino, 1-sulfo-6-(β-sulfatoethylsulfonyl)naphth-2-ylamino, 8-sulfo-6-(β-sulfatoethylsulfonyl)naphth-2-ylamino, 6-sulfo-8-(β-sulfatoethylsulfonyl)naphth-2-ylamino, 6-(β-sulfatoethylsulfonyl)naphth-2-ylamino and 8-(β-sulfatoethylsulfonyl)naphth-2-ylamino.

Further fiber-reactive radicals Z are, for example: 2,4-dichloro-1,3,5-triazin-6-yl, 2,4-difluoro-5-chloropyrimidin-6-yl, 2,4,5-trichloropyrimidin-6-yl, 2-methylsulfonyl-5-chloro-4-methylpyrimidin-6-yl, 5-cyano-2,4-dichloropyrimidin-6-yl, 4-methyl-2-fluoro-5-chloropyrimidin-6-yl, 2,3-dichloroquinoxalin-6-carbonyl and 2,4-difluoropyrimidin-6-yl, and furthermore radicals corresponding to the formula (8a)

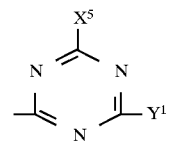

(8a)

in which $X^4$ is chlorine, fluorine or cyanoamino, A has one of the abovementioned particularly preferred meanings, $R^2$ is hydrogen, ethyl, methyl, β-hydroxyethyl, β-sulfatoethyl, phenyl, 3-sulfophenyl or 4-sulfophenyl and $W^1$ is 1,2-ethylene, 1,3-propylene, 2-methyl-1,2-ethylene, 2-methyl-1,3-propylene, 2-ethoxy-ethylene, 1,4phenylene, 1,3-phenylene, 2-methoxy-1,5-phenylene, 2,5-dimethoxy-1,4-phenylene, 2-methoxy-5-methyl-1,4-phenylene, 2-sulfo-1,4-phenylene, 2-hydroxy-1,5-phenylene, 2-bromo-1,5-phenylene or 4-2'-eth)phen-1,1'-ylene, where in these groups the 1-position is bonded with the N atom, or 1-sulfo-naphth-2,6-ylene, 6-sulfo-naphth-2,8-ylene, naphth-2,6-ylene or naphth-2,8-ylene, where in these groups the 2-position is bonded with the N atom, and furthermore radicals corresponding to the formula (8b)

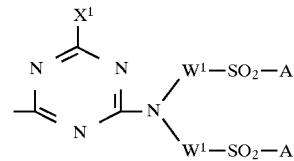

(8b)

in which $X^1$ and A have one of the abovementioned particularly preferred meanings and $W^1$ has one of the abovementioned meanings, and is preferably 1,3-propylene or 1,2-ethylene, and moreover groups corresponding to the formula (8c)

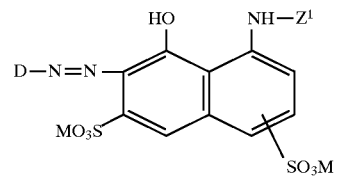

(8c)

in which $X^5$ is chlorine or fluorine and $Y^1$ is amino, methylamino, ethylamino, dimethylamino, diethylamino, bis-(β-hydroxyethyl)-amino, β-hydroxyethylamino, phenylamino, 3-sulfophenylamino, 4-sulfophenyl-amino, 2-sulfophenylamino, 2,5-disulfophenylamino, 2,4-disulfophenylamino, 2-carboxyphenylamino, 4-carboxyphenylamino, 2-sulfo-4-methoxy-phenylamino, 2-sulfo-4-methylphenylamino, 3-sulfo-4-methylphenylamino, 2-methylphenylamino, 3-methylphenylamino, 4-methylphenylamino, 2,5-dimethylphenylamino, 2,4-dimethylphenylamino, 2-methoxyphenylamino, 3-methoxyphenylamino, 4-methoxyphenylamino, 2- or 3- or 4-ethoxyphenylamino, N-ethylphenylamino, N-methylphenylamino, N-(β-hydroxyethyl)phenylamino, 2-chlorophenylamino, 3- or 4-chlorophenylamino, 2,5-dichlorophenylamino, naphth-2-ylamino, 1-sulfo-naphth-2-ylamino, 3,6,8-trisulfonaphth-2-ylamino, 4,6,8-trisulfonaphth-2-ylamino, 4,8-disulfonaphth-2-ylamino, 1,5-disulfonaphth-2-ylamino, N-morpholino, N-piperidino, N-piperazino, N-pyrrolidino, N'-(β-sulfatoethyl)-N-piperazino or N'-(β-hydroxyethyl)-N-piperazino.

Particularly preferred azo compounds of the formula (1) according to the invention are those of the formula (1A)

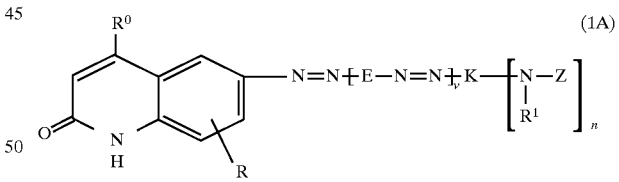

(1A)

in which $R^o$ is hydrogen or methyl, R is hydrogen, methyl, methoxy, chlorine, bromine or sulfo and E, v, K, $R^1$, Z and n have one of the abovementioned particularly preferred meanings.

Of these, azo compounds which are to be singled out in particular are those which correspond to the formulae (9a), (9b), (9c) and (9d)

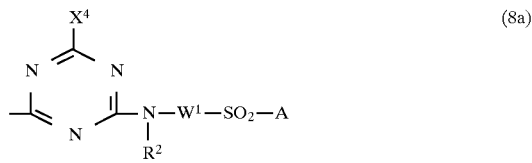

(9a)

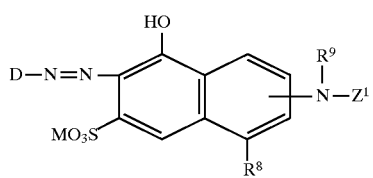
(9b)

$D-N=N-E^1-NH-Z^2$ (9c)

$D-N=N-E^1-N=N-E^2-NH-Z^2$ (9d)

in which:

D is a group of the formula (1b)

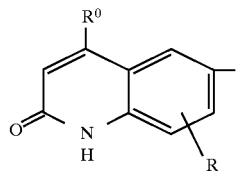
(1b)

in which $R^o$ and R have the meanings given for the formula (1), and preferably the meanings given for the formula (1A), and is, in particular, the 4-methyl-quinolin-2-ol-6-yl group;

M has the abovementioned meaning;

$R^8$ is hydrogen or sulfo;

$R^9$ is hydrogen, alkyl having 1 to 4 carbon atoms, such as methyl or ethyl, which can be substituted by 1 or 2 substituents from the group consisting of hydroxy, sulfo, carboxy and sulfato, or is phenyl, which can be substituted by 1, 2 or 3 substituents from the group consisting of sulfo and carboxy, and is preferably hydrogen;

the group —$SO_3M$ in formula (9a) is bonded in the para- or, preferably, in the meta-position relative to the group —$N(R^9)$—$Z^1$ and in formula (9b) is bonded in the ortho- or meta-position relative to $R^8$;

$E^1$ is 1,4-phenylene, which can be substituted by 1 or 2 substituents from the group consisting of sulfo, methyl, methoxy, ureido and acetylamino, or is 1,4-naphthylene, which can be substituted by a sulfo group in the 6-, 7- or 8-position, preferably 6- or 7-position;

$E^2$ is 1,4-phenylene, which can be substituted by one or two substituents from the group consisting of sulfo, methyl, methoxy, ureido and acetylamino, or is 1,4-naphthylene, which can be substituted by a sulfo group in the 6-, 7- or 8-position, preferably 6- or 7-position;

$Z^1$ is a radical of the formula (10A) or (10B) mentioned and defined below and $Z^2$ is a radical of the formula (10C) mentioned and defined below

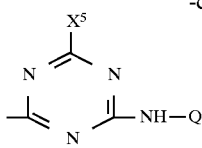
(10A)

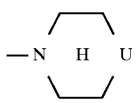
(10B)

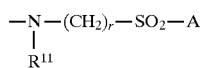
(10C)

in which $X^5$ is chlorine or fluorine, $Y^5$ is phenylamino, which can be substituted by 1 or 2 sulfo groups or a group of the formula —$SO_2$—A, where A has the abovementioned meaning, or by 1 or 2 sulfo groups and one of these groups —$SO_2$—A, or is naphthylamio, preferably naphth-2-ylamino, which can be substituted by 1, 2 or 3 sulfo groups or by a group of the formula —$SO_2$—A, where A has the abovementioned meaning, or by 1 or 2 sulfo groups and this group —$SO_2$—A, or is a group of the formula (11a), (11b) or (11c)

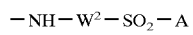
(11a)

—N—$(CH_2)_r$—$SO_2$—A (11b)
|
$R^{11}$

—NH—$W^2$—$SO_2$—A (11c)

in which

U is —O—, —S—, —$SO_2$— or —NH—, or is a group of the formula

in which $R^A$ is hydrogen, β-hydroxyethyl or β-sulfatoethyl, r is the number 2, 3 or 4, preferably 2 or 3, A has one of the abovementioned meanings, $R^{11}$ is hydrogen, methyl, ethyl, phenyl, monosulfophenyl, disulfophenyl or a radical of the formula —$(CH_2)_r$—$SO_2$—A where r and A have the abovementioned meanings, $W^2$ is alkylene having 3 to 6 C atoms, preferably 4 C atoms, which is interrupted by 1 or 2 hetero groups from the group consisting of the formulae —O—, —NH—, —$SO_2$— and —CO—, such as, for example, a group of the formula

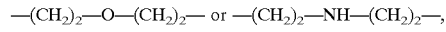

$G^1$ is hydrogen or chlorine,

Hal is chlorine or fluorine and

Q is phenyl, which can be substituted by 1, 2 or 3 sulfo groups or by a group of the formula —$SO_2$—A, where A has the abovementioned meaning, or by 1 or 2 sulfo groups, preferably 1 sulfo group, and this group —$SO_2$—A, or is naphthyl, preferably 2-naphthyl, which can be substituted by 1, 2 or 3 sulfo groups or by 1 group of the formula —$SO_2$—A, where A has the abovementioned meaning, or by 1 or 2 sulfo groups and this group —$SO_2$—A.

$Y^1$ is particularly preferably monosulfophenylamino, disulfophenylamino, monosulfophenylamino which is substituted by methoxy, methyl, carboxy, sulfo, hydroxyl, chlorine or bromine, a group of the formula (11c) of the abovementioned meaning, and of these preferably morpholino, or a group of the formula (11b), in which r and A have the meanings given and $R^{11}$ is phenyl or monosulfophenyl, or in which $R^{11}$ is a radical of the formula $—(CH_2)_r—SO_2—A$, where r and A have the abovementioned meaning.

The present invention furthermore relates to processes for the preparation of the azo compounds of the formula (1) according to the invention, which comprise diazotizing a compound of the formula (12)

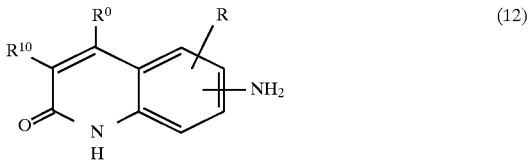
(12)

in which $R, R^o$ and $R^{10}$ have one of the abovementioned particularly preferred meanings, and coupling the diazotization product with a compound of the formula (13)

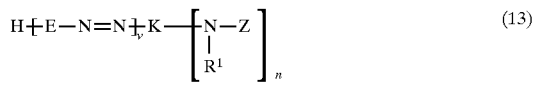
(13)

in which E, v, K, $R^1$, Z and n have one of the abovementioned, particularly preferred, meanings, or diazotizing a compound of the formula (14)

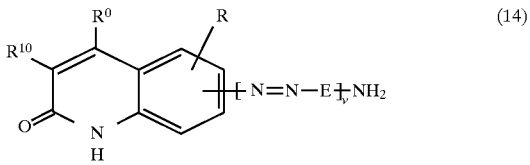
(14)

where R, $R^o$, $R^{10}$, E and v have one of the abovementioned, particularly preferred, meanings, and coupling the diazotization product with a compound of the formula H—K—Z, where K and Z have the abovementioned meaning, or reacting a compound of the formula (15)

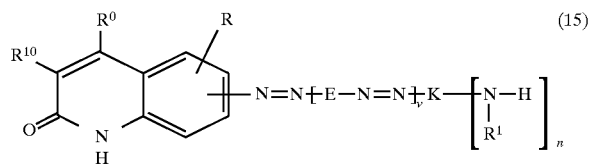
(15)

in which R, $R^o$, $R^{10}$, v, K, $R^1$ and n have one of the abovementioned, particularly preferred, meanings, with a compound of the formula $X^o$—Z, in which $X^o$ is chlorine, bromine or fluorine and Z has the abovementioned meaning, and of these, preferably with a compound of the formula (16)

(16)

in which $X^1$ and $Y^1$ have the abovementioned, particularly preferred, meanings and Hal is chlorine or fluorine.

The diazotization reactions are carried out by a procedure known per se in an aqueous medium at a pH of less than 2 and at a temperature of between −5° C. and +15° C. The coupling reactions are also carried out by a procedure known per se in aqueous solution or in an aqueous-organic medium at a pH of between 4 and 9, preferably between 5 and 7, and at a temperature of between 0° C. and 40° C., preferably between 5° C. and 25° C.

The condensation reactions between the compounds of the formula (15) and the fiber-reactive starting compound of the formula $X^o$—Z, where $X^o$ and Z have the abovementioned meaning, such as, preferably, of the formula (16) defined above, are likewise carried out in an aqueous or aqueous-organic medium in suspension or solution. If these reactions are carried out in an aqueous-organic medium, the organic medium is, for example, acetone, dimethylformamide, dimethylsulfoxide or N-methylpyrrolidone. The hydrogen halide liberated during the reaction is advantageously neutralized continuously by addition of aqueous alkali metal or alkaline earth metal hydroxides, carbonates or bicarbonates. As a rule, the reaction is carried out at a temperature of between −5° C. and +95° C. and at a pH of between 3 and 11, preferably between 4 and 6, and in the case where $X^o$ or Hal is fluorine, preferably at a temperature of between 20° and 40° C. and at a pH of between 4 and 10, particularly preferably between 4 and 7.

The starting compounds of the formula (12) are known from the literature (see, for example, Liebigs Ann. Chemie 559, 101,148 (1948), J. Med. Chem. 29, 2433 (1986) and J. Chem. Soc. 1930, 2346 and 2350); if individual compounds are not described, they can be prepared analogously to the procedure of the prior art. The other starting compounds, like the compounds of the formulae H—E—$NH_2$ and H—K—N($R^1$)H, and the fiber-reactive starting compounds of the formula $X^o$—Z are described in numerous instances in the literature and are often employed for the preparation of fiber-reactive dyestuffs (see, for example, European Patent Application Publication Nos. 0 541 057, 0 542 214 and 0 548 795) or they can be prepared analogously to the procedures described therein using corresponding starting compounds.

Starting compounds of the formula (12) are, for example, 4methyl-6-aminoquinolin-2-ol, 4-ethyl-6-aminoquinolin-2-ol, 4-methyl-5-amino-quinolin-2-ol, 4-ethyl-5-aminoquinolin-2-ol, 4-carboxy-6-aminoquinolin-2-ol, 7-methoxy-4-methyl-6-aminoquinolin-2-ol, 7-sulfo-4-methyl-6-aminoquinolin-2-ol, 8-methoxy-4-methyl-6-aminoquinolin-2-ol, 5-bromo-6-amino-4-methylquinolin-2-ol, 3-bromo-6-amino-4-methyl-quinolin-2-ol, 5-chloro-6-amino-4-methylquinolin-2-ol, 3-chloro-6-amino-4-methylquinolin-2-ol, 8-chloro-6-amino-4-methylquinolin-2-ol, 8-methoxy-6-aminoquinolin-2-ol, 8-chloro-6-aminoquinolin-2-ol, 4-aminocarbonyl-6-aminoquinolin-2-ol and 4-ethoxycarbonyl-6-amino-quinolin-2-ol.

The starting compounds corresponding to the formulae (17a) and (17b)

(17a)

(17b)

where $R^2$, $R^6$, W and A have the abovementioned meanings, which are contained as amino radicals in the starting compounds of the formulae (13) and (16) and are used for synthesis thereof, are known in some cases, thus, for example, from European Patent Application Publication Nos. 0 070 806, 0 070 807, 0 374 758, 0 499 588, 0 541 057, 0 568 860 and 0 669 667 and from U.S. Pat. Nos. 4,908,436 and 5,138,041 and British Patent 1 576 237, or can be synthesized analogously to the instructions given in these specifications.

Starting compounds of the formulae (17a) and (17b) are, for example N-[γ-(β'-chloroethylsulfonyl)propyl]amine, N-[γ-(β'-sulfatoethylsulfonyl)-propyl]amine, N-[γ-(vinylsulfonyl)propyl]amine, N-[β-(β'-chloroethyl-sulfonyl)ethyl]amine, N-[β-(β'-sulfatoethylsulfonyl)ethyl]amine, N-[β-(vinylsulfonyl)ethyl]amine, N-methyl-N-[β-(β'-chloroethylsulfonyl)-ethyl]amine, N-ethyl-N-[β-(β'-chloroethylsulfonyl)propyl]amine, N-n-propyl-N-[β-(β'-chloroethylsulfonyl)ethyl]amine, N-n-butyl-N-[β-(β'-chloro-ethylsulfonyl)ethyl]amine, N-carboxymethyl-N-[β-(β'-bromoethylsulfonyl)ethyl]amine, N-sulfatomethyl-N-[β-(β'-chloroethylsulfonyl)ethyl]amine, N-(β-carboxyethyl)-N-[β'-(β"-chloroethylsulfonyl)ethyl]amine, N-(β-sulfatoethyl)-N-[β'-(β"-chloroethylsulfonyl)ethyl]amine, N-(β-ethoxyethyl)-N-[β'-(β"-chloroethylsulfonyl)ethyl]amine, N-phenyl-N-[β-(β'-chloroethylsulfonyl)ethyl]amine, N-(4-chlorophenyl)-N-[β-(β'-chloroethylsulfonyl)ethyl]amine, N-(2-methylphenyl)-N-[β-(β'-chloroethylsulfonyl)-ethyl]amine, N-(4-methoxyphenyl)-N-[β-(β'-chloroethylsulfonyl)ethyl]amine, N-(3-sulfophenyl)-N-[β-(β'-chloroethylsulfonyl)ethyl]amine, N-(4-sulfophenyl)-N-[β-(β'-chloroethylsulfonyl)ethyl]amine, N-(β-cyanoethyl)-N-[β'-(β"-chloroethylsulfonyl)ethyl]amine, N-phenyl-N-(β-vinylsulfonylethyl)amine, N-(4-chlorophenyl)-N-(β-vinylsulfonylethyl)amine, N-(2-methylphenyl)-N-(β-vinylsulfonyl-ethyl)amine, N-(4-methoxyphenyl)-N-(β-vinylsulfonylethyl)amine, N-(3-sulfophenyl)-N-(β-vinylsulfonylethyl)-amine, N-(4-sulfophenyl)-N-(β-vinylsulfonylethyl)amine, N-phenyl-N-[β-(β'-sulfatoethylsulfonyl)-ethyl]amine, N-(4-chlorophenyl)-N-[β-(β'-sulfatoethylsulfonyl)ethyl]amine, N-(2-methylphenyl)-N-[β-(β'-sulfatoethylsulfonyl)ethyl]amine, N-(4-methoxyphenyl)-N-[β-(β'-sulfatoethylsulfonyl)ethyl]amine, N-(3-sulfophenyl)-N-[β-(β'-sulfatoethylsulfonyl)ethyl]amine, N-(4-sulfophenyl)-N-[β-(β'-sulfatoethylsulfonyl)ethyl]amine, N-methyl-N-[γ-(β'-chloroethylsulfonyl)propyl]amine, N-ethyl-N-[γ-(β'-chloroethylsulfonyl)propyl]amine, N-n-propyl-N-[γ-(β'-chloroethylsulfonyl)-propyl]amine, N-n-butyl-N-[γ-(β'-chloroethylsulfonyl)propyl]amine, N-carboxymethyl-N-[γ-(β'-bromethylsulfonyl)propyl]amine, N-sulfatomethyl-N-[γ-(β'-chloroethylsulfonyl)propyl]amine, N-(β-carboxyethyl)-N-[γ'-(β"-chloroethylsulfonyl)propyl]amine, N-(β-sulfatoethyl)-N-[γ'-(β"-chloroethylsulfonyl)propyl]amine, N-(β-sulfatoethyl)-N-[δ-(β"-chloroethylsulfonyl)butyl]amine, N-(β-ethoxyethyl)-N-[δ'-(β"-chloroethylsulfonyl)butyl]amine, N-(β-ethoxyethyl)-N-[γ'-(β"-chloroethylsulfonyl)propyl]amine, N-phenyl-N-[γ-(β'-chloroethylsulfonyl)propyl]amine, N-(4-chlorophenyl)-N-[γ-(β'-chloroethylsulfonyl) propyl]amine, N-(2-methylphenyl)-N-[γ-(β'-chloroethylsulfonyl)propyl]amine, N-(4-methoxyphenyl)-N-[γ-(β'-chloroethylsulfonyl)propyl]amine, N-(3-sulfophenyl)-N-[γ-(β'-chloroethylsulfonyl)-propyl]amine, N-(4-sulfophenyl)-N-[γ-(β'-chloroethylsulfonyl)propyl]amine, N-(β-cyanoethyl)-N-[γ'-(β"-chloroethylsulfonyl)propyl]amine, N-phenyl-N-(γ-vinylsulfonylpropyl)amine, N-(4-chlorophenyl)-N-(γ-vinylsulfonylpropyl)amine, N-(2-methylphenyl)-N-(γ-vinylsulfonylpropyl)amine, N-(4-methoxyphenyl)-N-(γ-vinylsulfonylpropyl)amine, N-(3-sulfophenyl)-N-(γ-vinylsulfonylpropyl)amine, N-(4-sulfophenyl)-N-(γ-vinylsulfonylpropyl)amine, N-phenyl-N-[γ-(β'-sulfatoethylsulfonyl)-propyl]amine, N-(4-chlorophenyl)-N-[γ-(β'-sulfatoethylsulfonyl)propyl]amine, N-(2-methylphenyl)-N-[γ-(β'-sulfatoethylsulfonyl)propyl]amine, N-(4-methoxyphenyl)-N-[γ-(β'-sulfatoethylsulfonyl)propyl]amine, N-(3-sulfophenyl)-N-[γ-(β'-sulfatoethylsulfonyl) propyl]amine, N-(4sulfophenyl)-N-[γ-(β'-sulfatoethylsulfonyl)propyl]amine, N-phenyl-N-[α-carboxy-γ-(β'-chloroethylsulfonyl)propyl]amine, N-phenyl-N-[α-ethoxycarbonyl-γ-(β'-chloroethylsulfonyl)propyl]amine, N-phenyl-N-[α-methoxycarbonyl-γ-(β'-chloroethylsulfonyl)propyl]amine, N-phenyl-N-[β-methyl-γ-(β'-chloroethylsulfonyl)propyl]amine, N-phenyl-N-[β-ethyl-γ-(β'-chloroethylsulfonyl)propyl]amine, N-phenyl-N-[δ-(β'-chloroethyl-sulfonyl)butyl]amine, N-phenyl-N-[ε-(β'-chloroethylsulfonyl)pentyl]amine, N-phenyl-N-[β-(β'-chloroethylsulfonyl)hexyl]amine, 3- and 4-(β-sulfato-ethylsulfonyl)aniline, 2-methoxy-5-(β-sulfatoethylsulfonyl)-aniline, 2,5-dimethoxy-4-(β-sulfatoethylsulfonyl)aniline, 2-methoxy-5-methyl-4-(β-sulfatoethylsulfonyl)aniline, 2-sulfo-4-(β-sulfatoethylsulfonyl)aniline, 2-hydroxy and 2-bromo-5-(β-sulfatoethylsulfonyl)aniline, 4-[β-(β'-sulfatoethylsulfonyl)ethyl]aniline, 1-sulfo-6-(β-sulfatoethylsulfonyl)-2-naphthylamine, 8-sulfo-6-(β-sulfatoethylsulfonyl)-2naphthylamine, 6-sulfo-8-(β-sulfatoethylsulfonyl)-2-naphthylamine and 8- and 6-(β-sulfatoethyl-sulfonyl)-2-naphthylamine.

Starting compounds which are used first as the coupling component and then, in the form of the amino-azo compound formed, as the diazo compound for the preparation of dis- and trisazo compounds of the formula (1) according to the invention and correspond to the formula H—E—NH$_2$ are, for example, aniline, 3-methylaniline, 2-methoxy-5-methyl-aniline, 2,5-dimethylaniline, 3-ureidoaniline, 3-acetylaminoaniline, 3-propionylaminoaniline, 3-butyrylaminoaniline, 3-methoxyaniline, 2-methyl-5-acetylaminoaniline, 2-methoxy-5-acetylaminoaniline, 2-methoxy-5-methylaniline, 3-(hydroxyacetylamino) aniline, 1,3-diaminobenzene, 1,3-diaminobenzene-4-sulfonic acid, 2- and 3-sulfoaniline, 3-hydroxyaniline, 1-aminonaphthalene-6-, -7- or -8-sulfonic acid, 1-amino-2-methoxynaphthalene-6-sulfonic acid, 2-amino-5-hydroxynaphthalene-7-sulfonic acid, 2-amino-5-hydroxynaphthalene-1,7-disulfonic acid, 2-amino-8-hydroxynaphthalene-6-sulfonic acid, 2-(4'-aminobenzoylamino)-5-naphthol-7-sulfonic acid, 1-(4'-amino-2'-sulfophenyl)-3-methyl-5-pyrazolone, 1-(4'-amino-2'-sulfophenyl)-3-carboxy-5-pyrazolone and N-(acetoacetyl)-3-sulfo-4-aminoanilide.

Coupling components corresponding to the formula H—K—N(R$^1$)H, which can be used for building up the azo compounds according to the invention and into the amino groups of which the radical of the fiber-reactive grouping can be introduced, are, for example, aniline, 3-methylaniline, 2,5-dimethylaniline, 2,5-dimethoxyaniline, 3-methoxyaniline, 3-acetylaminoaniline, 3-propionylaminoaniline, 3-butyrylaminoaniline, 3-benzoylaminoaniline, 3-(hydroxyacetylamino)aniline, 3-ureidoaniline, 2-methyl-5-acetylaminoaniline, 2-methoxy-5-acetylaminoaniline, 2-methoxy-5-methylaniline, 1-aminonaphthalene-6-sulfonic acid, 1-aminonaphthalene-7-sulfonic acid, 4-sulfo-1,3-diaminobenzene, 6-sulfo-2-methoxy-1-aminonaphthalene, 5,7-disulfo-2-aminonaphthalene, 1-amino-8-hydroxynaphthalene-4sulfonic acid, 1-amino-8-hydroxynaphthalene-6-sulfonic acid, 1-amino-8-hydroxynaphthalene-2,4-disulfonic acid, 1-amino-8-naphthol-3,6-disulfonic acid, 1-amino-8-hydroxy-4,6-disulfonic acid, 1-amino-8-hydroxynaphthalene-2,4,6-trisulfonic acid, 2-(methylamino)- and 2-(ethylamino)-5-hydroxynaphthalene-7-sulfonic acid, 2-amino-5-hydroxynaphthalene-1,7-disulfonic acid, 2-(methylamino)- and 2-(ethylamino)-8-hydroxynaphthalene-6-sulfonic acid, 2-amino-8-hydroxynaphthalene-3,6-disulfonic acid, 2-(4'-amino-3'-sulfophenylamino)-5-hydroxynaphthalene-7-sulfonic acid, 1-amino-8-hydroxy-2-(phenylazo)-naphthalene-3,6-disulfonic acid, 1-amino-8-hydroxy-2-(4'-sulfophenyl-azo)naphthalene- 3,6-disulfonic acid, 1-amino-8-hydroxy-2-(2',5'-disulfo-phenylazo)naphthalene-3,6-disulfonic acid, 1-(β-aminoethyl)-3-cyano-4-methyl-6-hydroxypyrid-2-one, 1-(γ-aminopropyl)-3-sulfomethyl-4-methyl-6-hydroxypyrid-2-one, 1,3-diaminobenzene, 3-[N,N-di-(β-hydroxy-ethyl)]aminoaniline, 3-[N,N-di-(β-sulfatoethyl)]-amino-4-methoxyaniline, 3-(sulfobenzylamino)aniline, 3-(sulfobenzoylamino)-4-chloroaniline and 3-[N,N-di-(sulfobenzyl)]aminoaniline, 2-sulfo-5-acetylaminoaniline, 2-amino-5-naphthol-7-sulfonic acid, 2-amino-8-naphthol-6-sulfonic acid, 1-(4'-aminobenzoyl)amino-8-hydroxynaphthaline-3,6-disulfonic acid, 1-(4'-aminobenzoyl)amino-8-hydroxy-naphthaline-4,6-disulfonic acid, 1-(3'-aminobenzyl)amino-8-hydroxynaphthaline-3,6-disulfonic acid, 1-(3'-aminobenzoyl)amino-8-hydroxynaphthaline-4,6-disulfonic acid, 1-(2'-aminobenzoyl)amino-8-hydroxynaphthaline-3,6-disulfonic acid, 1-(2'-aminobenzoyl)amino-8-hydroxynaphthaline-4,6-disulfonic acid, 2-(3'-aminobenzoyl)-amino-5-hydroxynaphthaline-7-sulfonic acid, 2-(2'-aminobenzoyl)amino-5-hydroxynaphthaline-7-sulfonic acid, 2-(4'-aminobenzoyl)amino-8-hydroxynaphthaline-6-sulfonic acid, 2-(3'-aminobenzoyl)amino-8-hydroxynaphthaline-6-sulfonic acid, 2-(2'-aminobenzoyl)amino-8-hydroxynaphthaline-6-sulfonic acid, 2-(4'-aminobenzoyl)amino-5-naphthol-7-sulfonic acid, 1-(4'-amino- or 1-(4'-acetylamino-2-sulfophenyl)-3-methyl- or -3-carboxy-5-pyrazolone, N-(3-sulfo-4-amino) acetoacetylanilide, 1-(3'-aminobenzoyl)- or 1-(4'-aminobenzoyl)amino-8-naphthol-3,6- or -4,6-disulfonic acid, 1-acetylamino-8-naphthol-3,6- or -4,6-disulfonic acid, 2-acetylamino-5-naphthol-7-sulfonic acid, 2-acetylamino-8-naphthol-6-sulfonic acid, 3-acetylamino-8-naphthol-6-sulfonic acid, 3-(N-methylamino)-8-naphthol-6-sulfonic acid, 1-(3'-amino- or 1-(3'-acetylamino-6'-sulfophenyl)-3-methyl- or -3-carboxy-5-pyrazolone, 2-(N-methyl-N-acetylamino) or 2-methylamino-5-naphthol-7-sulfonic acid, N-methylaniline and N-propyl-m-toluidine.

The azo compounds of the formula (1) prepared according to the invention are separated out of the synthesis batches by generally known methods, either by precipitation from the reaction medium by means of electrolytes, such as, for example, sodium chloride or potassium chloride, or by evaporation of the reaction solution, for example by spray drying, it being possible for a buffer substance to be added to this reaction solution.

The azo compounds of the formula (1)—called subsequently dyestuffs (1)—are suitable for dyeing and printing the most diverse materials, such as carboxamide groups containing materials, such as silk, leather, wool, polyamide fibers and polyurethanes, and in particular all types of cellulosic fiber materials. Such fiber materials are, for example, the naturally occurring cellulosic fibers, such as cotton, linen and hemp, as well as cellulose and regenerated cellulose. The dyestuffs (1) are also suitable for dyeing or printing fibers containing hydroxy groups which are contained in blend fabrics, for example mixtures of cotton with polyester fibers or polyamide fibers.

The dyestuffs (1) can be applied to the fiber material and fixed on the fiber in various ways, in particular in the form of aqueous dyestuff solutions and printing pastes. They are suitable both for the exhaust process and for dyeing by the pad-dyeing process, in which the goods are impregnated with aqueous dyestuff solutions, which contain salts if appropriate, and the dyestuff is fixed, after an alkali treatment or in the presence of alkali, if appropriate under the action of heat. The dyestuffs (1) are particularly suitable for the so-called cold pad-batched process, in which the dyestuff is applied to the padder together with the alkali and is then fixed by storage at room temperature for several hours. After fixing, the dyeings or prints are rinsed thoroughly with cold and hot water, if appropriate with the addition of an agent which has a dispersing action and promotes diffusion of the non-fixed portions. These dyeing and printing processes are described in numerous instances in the general technical literature and also in the patent literature, such as, for example, in the publications mentioned above.

The present invention therefore also relates to the use of the dyestuffs (1) for dyeing (including printing) these materials and to processes for dyeing (and printing) such materials by a procedure which is customary per se, in which a dyestuff (1) is employed as the colorant, by applying the dyestuff (1) to the material in an aqueous medium and fixing it on the material by means of heat or by means of a compound having an alkaline action or by means of both.

The dyestuffs (1) are distinguished by a high reactivity, a good fixing capacity and a very good build-up capacity. They can therefore be employed by the exhaust dyeing process at low dyeing temperatures and require only short steam times in the pad-steam processes. The degrees of fixing are high, and the non-fixed portions can easily be washed out, the difference between the degree of exhaustion and degree of fixing being remarkably low, i.e. the soaping loss being very low. The dyestuffs (1) are also particularly suitable for printing, above all on cotton, but also for printing nitrogen-containing fibers, for example wool or silk, or blend fabrics which contain wool or silk.

The dyestuffs (1) are also particularly suitable for low-salt exhaust dyeing processes, wherein the dye liquor comprises one or more electrolyte salts, such as sodium chloride, potassium chloride and sodium sulfate, in a total of 5 to 40 g/l (instead of the 50 to 80 g/l customary in the art). In spite of this low electrolyte salt concentration in the exhaust dye liquor, the dyestuffs (1) are absorbed uniformly and in a high tinctorial strength onto the fiber material, as a result of which level and strong dyeings are obtained. The high levelness of the dyeings exists with low-salt dyeing even if pale color shades are desired and the dyestuffs (1) are therefore used in only small amounts in the dye liquor. As a result of the possibility of low-salt dyeing with the dyestuffs (1), there is an advantage in their use, in particular in the ecological aspect. Even with a reduced amount of salt, the dyestuffs (1) show an unchanged tinctorial strength, which is particularly remarkable for fiber-reactive dyestuffs, since fiber-reactive dyestuffs as a rule suffer a loss of tinctorial strength if the amount of salt in the color bath or the dye liquor is reduced.

The dyeings and prints produced with the dyestuffs (1) have, in particular on cellulosic fiber materials, a high tinctorial strength and a high fiber-dyestuff bond stability, both in the acid and in the alkaline range, and furthermore a good fastness to light and very good wet-fastness properties, such as fastnesses to washing, water, seawater, crossdyeing and perspiration, as well as a good fastness to pleating, fastness to ironing and fastness to rubbing.

The following Examples serve to illustrate the invention. The parts are parts by weight and the percentage data are percentages by weight, unless noted otherwise. Parts by weight bear the same relation to parts by volume as the kilogram to the liter.

The compounds described by formulae in the Examples are given in the form of the free acid; in general, they are prepared and isolated in the form of their alkali metal salts, such as lithium, sodium or potassium salts, and are used for dyeing in the form of their salts. The starting compounds and components mentioned in the form of the free acid in the following Examples, in particular the Tabular Examples, can also be employed in the synthesis as such or in the form of their salts, preferably alkali metal salts.

The absorption maxima ($\lambda_{max}$) in the visible range stated for the compounds according to formula (1) were determined with the aid of their alkali metal salts in aqueous solution. In the Tabular Examples, the $\lambda_{max}$-values are in parentheses where the color shade is stated; the wavelength data are based on nm.

EXAMPLE 1 a) 50.6 parts of aniline-2,5-disulfonic acid are added to a suspension of 37.6 parts of cyanuric chloride in 2000 parts of water at a temperature between 0° and 3° C. and a pH of between 2 and 2.5 in the course of about 60 minutes. The batch is subsequently stirred for about a further 30 minutes and an aqueous suspension of 50 parts of 3-amino-8-hydroxy-6-sulfonaphthalene in 1000 parts of water is then added, a pH of 4.5 is established and the batch is heated to 40° C. and stirred for about a further 2 hours, while maintaining these conditions.

b) 60 parts of a 31% strength aqueous hydrochloric acid and 14 parts of sodium nitrite are added to 34.8 parts of 6-amino-4-methylquinolin-2-ol in 3000 parts of water at 0° C. to 5° C., while stirring thoroughly. The batch is subsequently stirred at this temperature for about a further 30 minutes and the diazonium salt solution thus obtained is then added to the solution, prepared under a) of the compound 3-N-[2'-(2'',5''-disulfophenyl)amino-4'-chloro-1',3', 5'-triazin-6'-yl]amino-8-hydroxy-6-sulfonaphthalene, which serves as the coupling component, in the course of about 15 minutes while maintaining a pH of between 6 and 7. The batch is subsequently stirred for about a further 12 hours, while maintaining this pH and at a temperature of between 20° and 25° C., and the resulting azo compound according to the invention which, written in the form of the free acid, corresponds to the formula is then isolated as an alkali metal salt (sodium salt) in the customary manner, for example by salting out with sodium chloride.

The monoazo compound according to the invention shows very good fiber-reactive dyestuff properties and produces strong red dyeings and prints with good fastness properties on the fiber materials mentioned in the description, in particular on cellulosic fiber materials, by the dyeing and printing processes customary in the art for fiber-reactive dyestuffs.

EXAMPLE 2

30 parts of an aqueous 31% strength hydrochloric acid and 6.9 parts of sodium nitrite are added to 17.4 parts of 6-amino-4-methylquinolin-2-ol in 600 parts of water at a temperature between 0° and 5° C., while stirring thoroughly. The batch is subsequently stirred at this temperature for a further 30 minutes and the resulting diazonium salt solution is then added to a solution of 54.5 parts of 1-N-(2'-morpholino-4'-fluoro-1',3',5'-triazin-6'-yl)amino-8-hydroxy-3,6-disulfonaphthalene (prepared according to European Patent Application Publication No. 0 542 082) in 1000 parts of water in the course of 15 minutes, and the batch is subsequently stirred for about a further 12 hours, while maintaining a pH of 7 and at a temperature of between 20° and 25° C.

The azo compound according to the invention which, written in the form of the free acid, has the formula

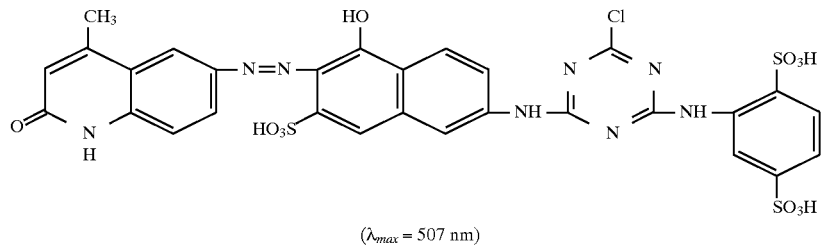

($\lambda_{max}$ = 507 nm)

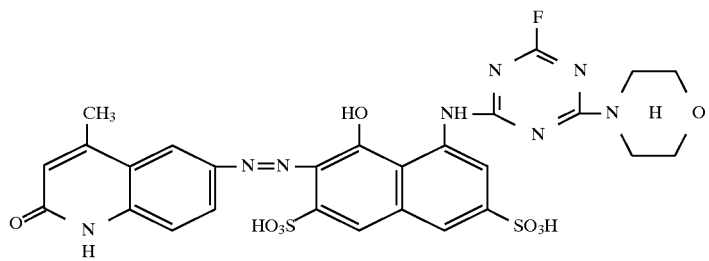

($\lambda_{max}$ = 525 nm)

is isolated as an alkali metal salt (sodium salt) from the synthesis solution in the customary manner, for example by salting out with sodium chloride. It shows very good fiber-reactive dyestuff properties and dyes, for example, cellulosic fiber materials in strong, brilliant, magenta-colored shades with a high degree of fixing by the customary application processes.

EXAMPLE 3

35 parts of 6-amino-4-methylquinolin-2-ol are diazotized in a mixture of 3000 parts of water and 60 parts of a 31% strength aqueous hydrochloric acid at a temperature of 0° to 5° C. by addition of 14 parts of sodium nitrite. The batch is subsequently stirred for about a further 30 minutes and the resulting diazonium salt solution is then added to a solution of 33.5 parts of 6-(2',4'-difluoropyrimidin-6'-yl)amino-3-sulfo-1-hydroxynaphthalene in 1000 parts of water in the course of about 15 minutes, while maintaining a pH of 6 to 7. The coupling reaction is brought to completion within this pH range at 20° to 25° C. in the course of about 12 hours, with further stirring, and the azo compound according to the invention, of the formula (written in the form of the free acid)

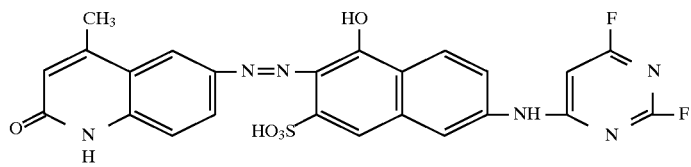

($\lambda_{max}$ = 500 nm)

is then isolated as an alkali metal salt (sodium salt) in the customary manner, for example by spray drying the aqueous synthesis solution or by salting out the compound from the synthesis solution with sodium chloride.

The azo compound according to the invention shows very good fiber-reactive dyestuff properties and dyes the materials mentioned in the description, in particular cellulosic fiber materials, such as cotton, in deep, scarlet-red shades with good fastness properties by the application processes customary in the art for fiber-reactive dyestuffs. With this azo compound according to the invention, it is particularly advantageous that the dyeing can be carried out with 5 to 15 g of sodium chloride or sodium sulfate per liter of dyebath or dye liquor without the tinctorial strength being reduced.

EXAMPLE 4

14.9 parts of 6-amino-4-methylquinolin-2-ol are diazotized in aqueous hydrochloric acid solution (600 parts of water and 30 parts of an aqueous 31% strength hydrochloric acid) at 0° to 5° C. by means of 6.9 parts of sodium nitrite. After addition of the sodium nitrite, the batch is subsequently stirred at 0° to 5° C. for a further 30 minutes and the resulting diazonium salt solution is added to a solution of 37.5 parts of 6-(2',4'-difluoro-5'-chloropyrimidin-6'-yl) amino-3-sulfo-1-hydroxynaphthalene in 800 parts of water. Stirring of the reaction batch is continued for about a further 12 hours, while maintaining a pH of about 7 and a temperature of 20° to 25° C., and the azo compound according to the invention is isolated in the customary manner.

It has, written in the form of the free acid, the formula

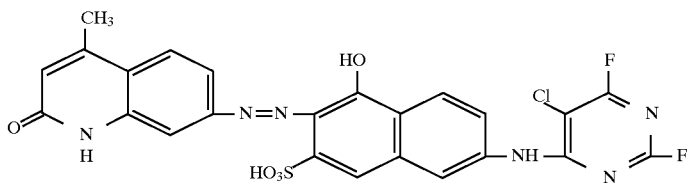

($\lambda_{max}$ = 506 nm)

and shows good fiber-reactive dyestuff properties. It dyes cotton, for example, in brilliant yellowish-tinged color shades with good fastness properties by the dyeing and printing processes customary in the art.

With this azo compound according to the invention, it is particularly advantageous that dyeing can be carried out with 5 to 15 g of sodium chloride or sodium sulfate per liter of dyebath or dye liquor without the tinctorial strength being reduced.

EXAMPLE 5

31.7 Parts of 3-amino-4,6-disulfo-8-hydroxynaphthalene are reacted with 19 parts of cyanuric chloride in 500 parts of water at a pH of between 2 and 2.5 and at a temperature between 0° and 5° C. in the course of 2 to 3 hours. 36 parts of bis-(β-chloroethylsulfonylethyl)amine hydrochloride are then added to the reaction mixture and the reaction is brought to completion at a pH of between 6 and 6.5 and a temperature between 40° and 50° C., while stirring. The batch is then allowed to cool to 20° to 25° C. and a diazonium salt solution, prepared according to Example 1, of 14 parts of 6-amino-4-methylquinolin-2-ol is then added, while maintaining a pH of between 6 and 6. Stirring is continued for about a further 12 hours and the azo dyestuff according to the invention which, written in the form of the free acid, has the formula and dyes, for example, cotton in scarlet-red color shades with good fastness properties.

EXAMPLE 6

A diazonium salt solution, prepared according to Example 1b), from 29.8 parts of 6-amino-4methylquinolin-2-ol is stirred into a solution of 51.1 parts of the sodium salt of the compound 1-N-(2',4'-dichloro-1',3',5'-triazin-6'-yl)-amino-8-hydroxy-3,6-disulfonaphthalene in 1000 parts of water and the coupling reaction is carried out at a temperature between 18° and 25° C. and a pH of 5 to 6. The azo compound according to the invention is isolated from the synthesis solution in the customary manner, for example by salting out with sodium chloride. It has, written in the form of the free acid, the formula

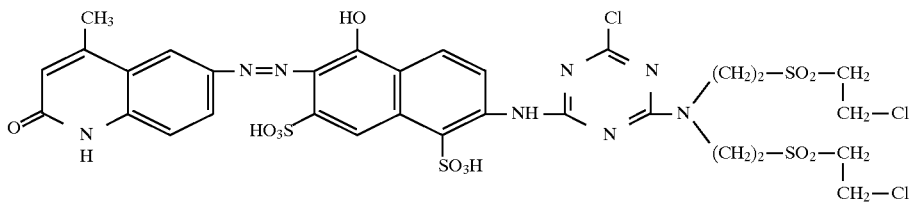

($\lambda_{max}$ = 510 nm)

is then isolated as an alkali metal salt in the customary manner. It shows very good fiber-reactive dyestuff properties

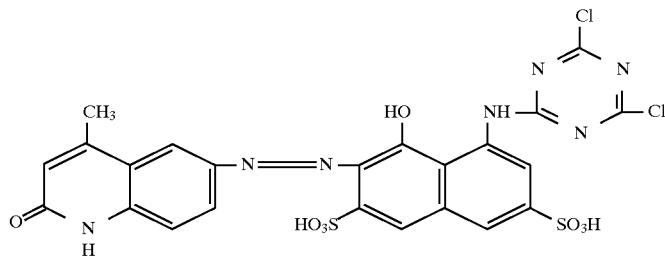

($\lambda_{max}$ = 525 nm)

shows very good fiber-reactive dyestuff properties and dyes, for example, cellulosic fiber materials in strong magenta-colored shades with a high degree of fixing by the dyeing processes customary in the art.

EXAMPLE 7

The diazonium salt solution prepared according to Example 1b) is stirred into a solution of 77.8 parts of the sodium salt of the compound 1-N-[2'-(4"-β-sulfatoethylsulfonyl)-4'-chloro-1',3',5'-triazin-6'-yl]amino-8-hydroxy -3,6-disulfonaphthalene in 500 parts of water, while maintaining a pH of 5 to 6. The coupling reaction is brought to completion at a pH of 5 to 6 and a temperature between 18° and 25° C. and the resulting azo compound according to the invention, of the formula (written in the form of the free acid)

EXAMPLE 8

A mixture of 17.4 parts of 6-amino-4-methylquinolin-2-ol, 800 parts of water and 30 parts of a 31% strength aqueous hydrochloric acid is stirred at 0° to 5° C. for a while, with thorough mixing, and 7.5 parts of sodium nitrite are then added. The mixture is subsequently stirred further for some time, until the diazotization has ended, excess nitrite is destroyed with a little amidosulfonic acid and the diazonium salt solution thus obtained is metered into a solution, of 25° C. and a pH of 5, of 79.9 parts of the compound of the formula

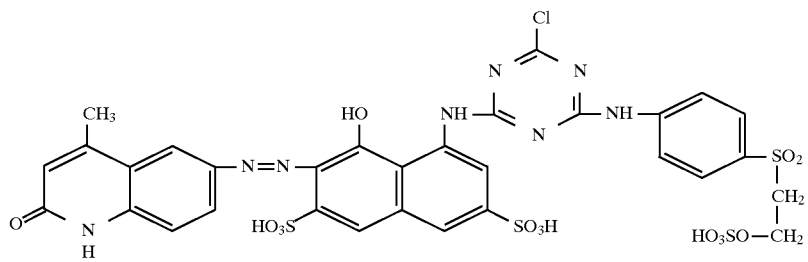

($\lambda_{max}$ = 528 nm)

is isolated, for example, by salting out with sodium chloride. The azo compound according to the invention, as a dyestuff with good fiber-reactive dyestuff properties, produces, for example on cellulosic fiber materials, strong magenta-colored dyeings and prints at a high degree of fixing.

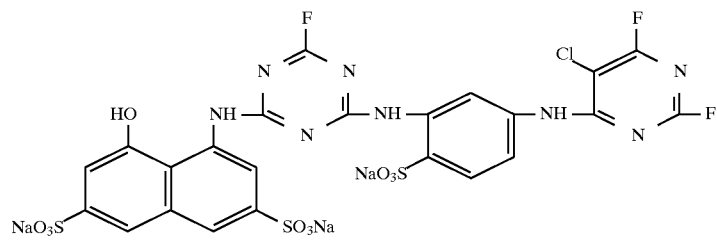

(known from EP-A-0 133 843) in 1000 parts of water. The coupling reaction is brought to completion in the course of 6 hours, while slowly heating the reaction batch to 30° C. and maintaining a pH range between 5 and 6.

The azo compound according to the invention, of the formula (written in the form of the free acid)

is isolated in the customary manner. It shows good fiber-reactive dyestuff properties and dyes, for example, cotton in strong, magenta-colored shades by the application processes customary for fiber-reactive dyestuffs; the resulting dyeings and prints have good fastness properties during use.

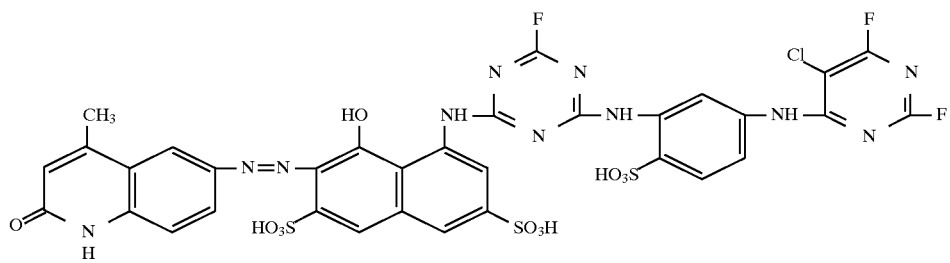

($\lambda_{max}$ = 528 nm)

is isolated as an alkali metal salt (sodium salt) in the customary manner, by salting out with sodium chloride or spray drying. It shows good fiber-reactive properties and dyes, for example, cotton in magenta-colored shades of high tinctorial strength by the application processes customary in the art for fiber-reactive dyestuffs; the resulting dyeings and prints have good fastness properties during use.

EXAMPLE 9

19.5 parts of 6-amino-8-chloroquinolin-2-ol (known from J. Med. Chem. 29, 2433 (1986)) are mixed thoroughly in 800 parts of water with 30 parts of an aqueous 31% strength hydrochloric acid at 0° to 5° C., while stirring vigorously; 7.5 parts of sodium nitrite are then added to this mixture. The mixture is subsequently stirred further for some time, until the diazotization has ended, excess nitrite is destroyed with a little amidosulfonic acid and the diazonium salt solution thus obtained is added slowly to a solution, of 10° to 15° C. and a pH of 4 to 5, of 54.5 parts of the coupling component employed in Example 2 and described therein in 1000 parts of water. The coupling reaction is carried out while heating slowly to 22° to 27° C. and maintaining a pH of between 4 and 5.

When the coupling reaction has ended, the azo compound according to the invention, of the formula (written in the form of the free acid)

EXAMPLE 10

A mixture of 16.0 parts of 6-aminoquinolin-2-ol, 800 parts of water and 30 parts of an aqueous 31% strength hydrochloric acid is stirred vigorously for a while, and 7.5 parts of sodium nitrite are then added. When the diazotization has ended, excess nitrous acid is destroyed in the customary manner, and the resulting diazonium salt solution is stirred slowly into a solution, of 10° to 15° C. and a pH of 4 to 5, of 51.8 parts of the compound 1-[2'-fluoro-4'-(N-ethyl-N-phenyl)aminotriazin-6'-yl]amino-8-hydroxy-3,6-disulfonaphthalene in 1000 parts of water. The coupling reaction is carried out while heating slowly to 22° to 27° C. and maintaining a pH of 4 to 5.

The azo compound according to the invention, of the formula (written in the form of the free acid)

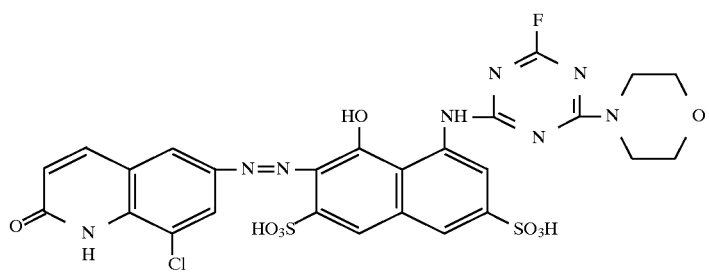

($\lambda_{max}$ = 517 nm)

65

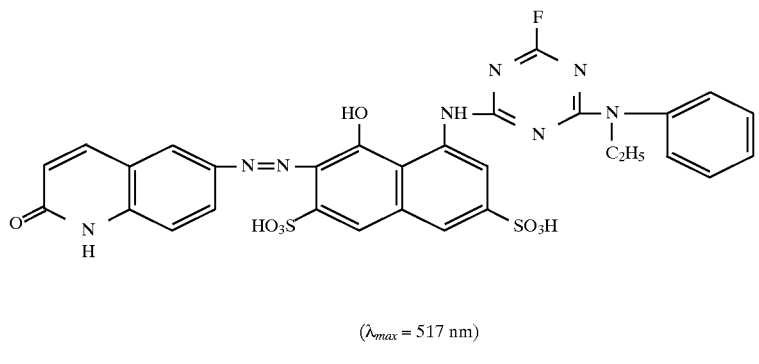

($\lambda_{max}$ = 517 nm)

is isolated in the customary manner. It gives, for example on cotton, strong dyeings with good fastness properties during use in a bluish-tinged red color shade by application and fixing processes customary in the art for fiber-reactive dyestuffs.

EXAMPLE 11

17.4 parts of 7-amino-4-methylquinolin-2-ol (known from Heterocyclic Chemistry 321, 158 (1990)) are diazotized analogously to the instructions of Example 10. The resulting diazonium salt solution is stirred into a solution, of 10° to 15° C. and a pH of 4 to 5, of 78.1 parts of the chlorotriazine compound employed and described in Example 7. The coupling reaction is carried out while heating slowly to 22° to 27° C. at a pH of 4 to 5.

The resulting azo compound according to the invention, of the formula

EXAMPLE 12

17.7 parts of 5-amino-8-methoxyquinolin-2-ol (known from J. Med. Chem. 29, 2427 (1986)) are diazotized in accordance with the instructions of Example 10. The resulting diazonium salt solution is stirred slowly into a solution, of 10° to 15° C. and a pH of 4 to 5, of 58.7 parts of the compound 1-[2'-chlor-4'-(3"-sulfophenyl)aminotriazin-6'-yl]amino-8-hydroxy-3,6-disulfo-naphthalene in 1000 parts of water, with thorough stirring. The coupling reaction is carried out in accordance with the instructions of Example 10.

The azo compound according to the invention, of the formula (written in the form of the free acid)

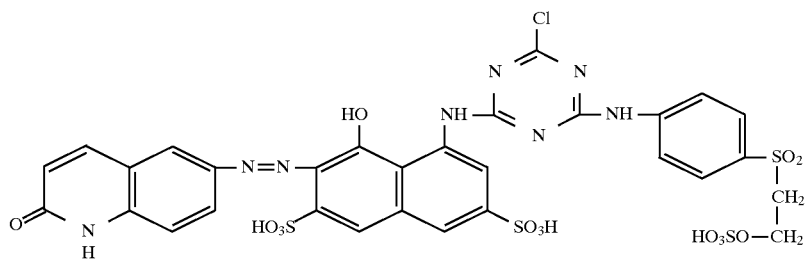

($\lambda_{max}$ = 511 nm)

is isolated in the customary manner; it produces, for example on cotton, strong red dyeings and prints with good fastness properties during use.

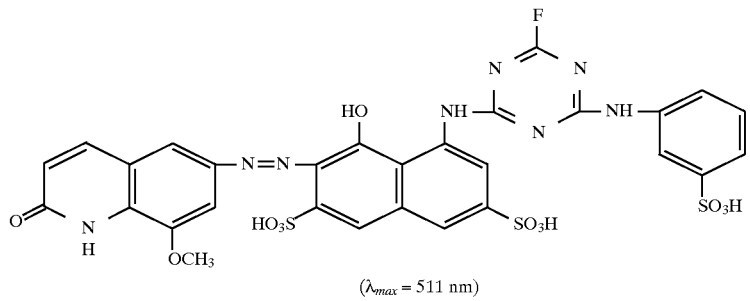

($\lambda_{max}$ = 511 nm)

which has been isolated from the synthesis solution in the customary manner, shows good fiber-reactive dyestuff properties and dyes, for example, cotton in strong red shades with good fastness properties during use.

EXAMPLES 13 to 32

Further azo compounds according to the invention, corresponding to the formula (A)

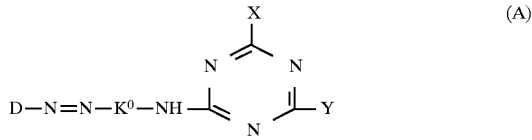

are described in the following Tabular Examples with the aid of the formula components thereof. They can be prepared in the manner according to the invention, for example in accordance with one of the above Examples, by means of the components which can be seen from the particular Tabular Example in association with the formula (A) (the diazo component D—NH$_2$, the coupling component H—K°—NH$_2$, cyanuric fluoride or cyanuric chloride, if appropriate an amino compound H—X and a compound H—Y). They have very good fiber-reactive dyestuff properties and produce strong, fast dyeings and prints in the color shade stated for dyeings on cottons in the particular Tabular Example on the materials mentioned in the description, in particular cellulosic fiber materials, such as cotton, by the known dyeing and printing processes.

| | | Azo compound of the formula (A) | | | |
|---|---|---|---|---|---|
| Example | Radical D- | Radical -K°- | Radical X | Radical Y | Colour shade |
| 13 | 4-methylquinoline-2-ol-6-yl | 3,6-disulfo-8-hydroxy-naphth-7,1-ylene | chloro | 4-(β-sulfatoethylsulfonyl)-phenylamino | violet (547) |
| 14 | 4-methylquinoline-2-ol-6-yl | 3,6-disulfo-8-hydroxy-naphth-7,1-ylene | fluoro | 3-sulfophenylamino | violet (551) |
| 15 | 4-methylquinoline-2-ol-6-yl | 6-sulfo-8-hydroxy-naphth-7,3-ylene | chloro | " | red (520) |
| 16 | 4-methylquinoline-2-ol-6-yl | 6-sulfo-8-hydroxy-naphth-7,3-ylene | chloro | 4,6,8-trisulfonaphth-2-yl-amino | red (520) |
| 17 | 4-methylquinoline-2-ol-6-yl | 6-sulfo-8-hydroxy-naphth-7,3-ylene | 3-sulfophenyl-amino | 4-(β-sulfatoethylsulfonyl)-phenylamino | red (520) |
| 18 | 4-methylquinoline-2-ol-6-yl | 6-sulfo-8-hydroxy-naphth-7,3-ylene | chloro | 2-sulfo-4-(β-sulfatoethylsulfonyl)-phenylamino | red (520) |
| 19 | 4-methylquinoline-2-ol-6-yl | 4,6-disulfo-8-hydroxy-naphth-7,3-ylene | chloro | 2-sulfo-4-(β-sulfatoethylsulfonyl)-phenylamino | rot (522) |
| 20 | 4-methylquinoline-2-ol-6-yl | 4,6-disulfo-8-hydroxy-naphth-7,3-ylene | fluoro | 3-(2',4'-difluoropyrimidin-6'-yl)-aminosulfophenlamino | red (519) |
| 21 | 4-methylquinoline-2-ol-6-yl | 6-sulfo-8-hydroxy-naphth-7,2-ylene | chloro | 2,5-disulfophenylamino | red (527) |
| 22 | 4-methylquinoline-2-ol-6-yl | 3,6-disulfo-8-hydroxy-naphth-7,1-ylene | chloro | " | bluish-tinged red (545) |
| 23 | 4-methylquinoline-2-ol-6-yl | 4,6-disulfo-8-hydroxy-naphth-7,3-ylene | chloro | N-phenyl-N-[(β'-sulfatoethyl-sulfonyl)propyl]amino | red (521) |
| 24 | 4-methylquinoline-2-ol-6-yl | 4,6-disulfo-8-hydroxy-naphth-7,3-ylene | chloro | γ-(β'-sulfatoethylsulfonyl)propyl-amino | red (520) |
| 25 | 4-methylquinoline-2-ol-6-yl | 4,6-disulfo-8-hydroxy-naphth-7,3-ylene | chloro | bis-[γ-(β'-sulfatoethylsulfonyl)-propyl]amino | red (519) |
| 26 | 4-methylquinoline-2-ol-6-yl | 6-sulfo-8-hydroxy-naphth-7,3-ylene | fluoro | morpholino | red (525 |
| 27 | 4-methylquinoline-2-ol-6-yl | 6-sulfo-8-hydroxy-naphth-7,3-ylene | fluoro | N-ethylphenylamino | red (526) |
| 28 | 4-methylquinoline-2-ol-6-yl | 6-sulfo-8-hydroxy-naphth-7,3-ylene | fluoro | 3-sulfophenylamino | red (525) |
| 29 | 4-methylquinoline-2-ol-6-yl | 6-sulfo-8-hydroxy-naphth-7,3-ylene | fluoro | 1-sulfonaphth-1-ylamino | red (522) |
| 30 | 4-carboxyquinoline- | 3,6-disulfo-8-hydroxy- | fluoro | morpholino | magenta |

| | Azo compound of the formula (A) | | | | |
|---|---|---|---|---|---|
| Example | Radical D- | Radical -K°- | Radical X | Radical Y | Colour shade |
| | 2-ol-6-yl | naphth-7,1-ylene | | | (537) |
| 31 | 3-chloro-4-methyl-quinoline-2-ol-6-yl | 3,6-disulfo-8-hydroxy-naphth-7,1-ylene | fluoro | morpholino | magenta (534) |
| 32 | 8-methoxyquinoline-2-ol-6-yl | 3,6-disulfo-8-hydroxy-naphth-7,1-ylene | fluoro | morpholino | magenta (536) |

EXAMPLES 33 to 37

Further azo compounds according to the invention, corresponding to the formula (B)

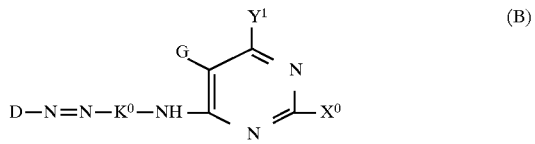

are described in the following Tabular Examples with the aid of their formula components. They can be prepared in the manner according to the invention, for example in accordance with one of the above Examples, by means of the components which can be seen from the particular Tabular Example in association with the formula (B) (the diazo component D—NH$_2$, the coupling component H—K$^O$—NH$_2$ and a halogen-substituted pyrimidine). They have very good fiber-reactive dyestuff properties and produce strong, fast dyeings and prints in the color shades stated for dyeings on cotton in the particular Tabular Example on the materials mentioned in the description, in particular cellulosic fiber materials, such as cotton, by the known dyeing and printing processes.

R is hydrogen, alkyl having 1 to 4 carbon atoms, alkoxy having 1 to 4 carbon atoms, halogen or sulfo;

R$^1$ is hydrogen, alkyl having 1 to 4 carbon atoms or alkyl having 1 to 4 carbon atoms which is substituted by hydroxy, cyano, alkoxy having 1 to 4 carbon atoms, carboxy, sulfo, sulfato or phosphato, or is phenyl or naphthyl, or is phenyl or naphthyl each being substituted by 1, 2 or 3 substituents selected from the group consisting of halogen, hydroxy, cyano, alkoxy having 1 to 4 carbon atoms, alkyl having 1 to 4 carbon atoms, alkoxycarbonyl having 2 to 5 carbon atoms, carboxy, sulfamoyl, sulfo and alkylsulfonyl with an alkyl having 1 to 4 carbon atoms;

E is the bivalent radical, which is free from the amino group, of a compound from the aniline or naphthylamine series which is capable of coupling and may be diazotized;

v is the number zero, 1 or 2;

K is the bivalent radical, which is free from the amino group, of a coupling component of the aniline or naphthylamine series or the bivalent radical of a coupling component of the heterocyclic series;

n is the number 1 or 2;

Z is a fiber-reactive grouping or group, where, if n is greater than 1, the radicals —N(R$^1$)—Z can have different meanings from one another;

| | Azo compound of the formula (B) | | | | | |
|---|---|---|---|---|---|---|
| Example | Radical D- | Radical -K°- | Radical G | Radical Y° | Radical X° | Color shade |
| 33 | 4-methylquinolin-2-ol-6-yl | 6-sulfo-8-hydroxynaphth-7,3-ylene | cyano | chloro | chloro | red (501) |
| 34 | " | 6-sulfo-8-hydroxynaphth-7,3-ylene | chloro | chloro | chloro | red (506) |
| 35 | " | 6-sulfo-8-hydroxynaphth-7,3-ylene | methyl | chloro | methylsulfonyl | red (504) |
| 36 | quinolin-2-ol-6-yl | 6-sulfo-8-hydroxynaphth-7,3-ylene | chloro | fluoro | fluoro | red (502) |
| 37 | 8-chloroquinolin-2-ol-6-yl | 6-sulfo-8-hydroxynaphth-7,3-ylene | hydrogen | fluoro | fluoro | red (505) |

I claim:

1. An azo compound corresponding to the formula (1)

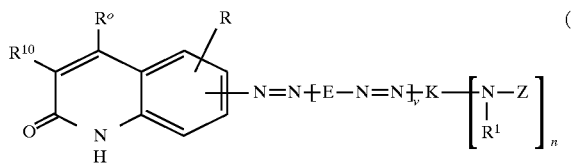

in which:

R° is hydrogen, alkyl having 1 to 4 carbon atoms, halogen, sulfo, carboxy, aminocarbonyl, alkoxycarbonyl having 2 to 5 carbon atoms or phenyl;

R$^{10}$ is hydrogen, alkyl having 1 to 4 carbon atoms or halogen;

the compounds of the formula (1) have at least one sulfo group.

2. An azo compound as claimed in claim 1 in which R° is hydrogen or alkyl of 1 to 4 carbon atoms.

3. An azo compound as claimed in claim 1 in which R$^{10}$ is hydrogen.

4. An azo compound as claimed in claim 1 in which R is hydrogen.

5. An azo compound as claimed in claim 1, in which R° is methyl and R and R$^{10}$ are both hydrogen.

6. An azo compound as claimed in claim 1, in which Z is a group of the formula (3a), (3b) or (3c)

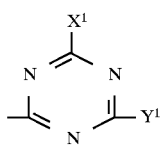

(3a)

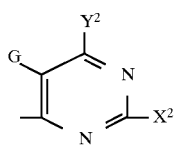

(3b)

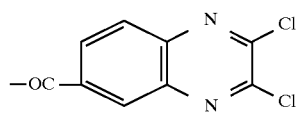

(3c)

in which:

X¹ is halogen or cyanoamino or a group of the formula (4)

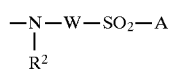

(4)

in which

R² is hydrogen or alkyl having 1 to 4 carbon atoms or alkyl having 1 to 4 carbon atoms which is substituted by hydroxy, cyano, alkoxy having 1 to 4 carbon atoms, carboxy, sulfo, sulfato or phosphato, or is phenyl or naphthyl, or is phenyl or naphthyl each being substituted by 1, 2 or 3 substituents selected from the group consisting of halogen, hydroxy, cyano, alkoxy having 1 to 4 carbon atoms, alkyl having 1 to 4 carbon atoms, alkoxycarbonyl having 2 to 5 carbon atoms, carboxy, sulfamoyl, sulfo and alkylsulfonyl with an alkyl having 1 to 4 carbon atoms, W is alkylene having 2 to 4 carbon atoms, or is alkylene having 3 to 6 carbon atoms which is interrupted by 1 or 2 hetero groups selected from the group consisting of the formulae —O—, —NH—, —SO₂—, —CO— and —N(R^A)— where R^A is hydrogen, alkyl having 1 to 4 carbon atoms, phenyl, naphthyl, or phenyl or naphthyl each being substituted by 1 to 3 substituents selected from the group consisting of sulfo, carboxy, alkoxy having 1 to 4 carbon atoms, alkyl having 1 to 4 carbon atoms, halogen, cyano and nitro, or W is phenylene or naphthylene, or is phenylene or naphthylene each being substituted by 1, 2 or 3 substituents selected from the group consisting of halogen, hydroxy, cyano, nitro, alkoxy having 1 to 4 carbon atoms, alkyl having 1 to 4 carbon atoms, alkoxycarbonyl having 2 to 5 carbon atoms, carboxy, sulfamoyl and sulfo, or is phenylenealkylene or alkylenephenylene, each with an alkylene having 1 to 4 carbon atoms, and A is vinyl, or is ethyl which is substituted in the β-position by a substituent which is split off by means of an alkali to form the vinyl group;

Y¹ is chlorine or a group of the formula (5)

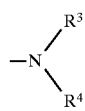

(5)

in which

R³ is hydrogen or alkyl having 1 to 4 carbon atoms, or is alkyl having 1 to 4 carbon atoms which is substituted by halogen, hydroxy, cyano, alkoxy having 1 to 4 carbon atoms, alkoxycarbonyl having 2 to 5 carbon atoms, carboxy, sulfo, sulfato or phosphato, or is a group of the formula —W—SO₂—A where W and A have one of the abovementioned meanings, and R⁴ is hydrogen or alkyl having 1 to 4 carbon atoms, or is alkyl having 1 to 4 carbon atoms which is substituted by halogen, hydroxy, cyano, alkoxy having 1 to 4 carbon atoms, alkoxycarbonyl having 2 to 5 carbon atoms, carboxy, sulfo, sulfato or phosphato, or is cycloalkyl having 5 to 8 carbon atoms or a group of the formula —W—SO₂—A where W and A have one of the abovementioned meanings, or is phenyl or naphthyl, or is phenyl or naphthyl each being substituted by 1, 2 or 3 substituents selected from the group consisting of halogen, hydroxy, cyano, alkoxy having 1 to 4 carbon atoms, alkyl having 1 to 4 carbon atoms, alkoxycarbonyl having 2 to 5 carbon atoms, carboxy, sulfamoyl, sulfo and alkylsulfonyl with an alkyl having 1 to 4 carbon atoms, or R³ and R⁴ together are an alkylene having 3 to 6 carbon atoms, or an alkylene having 3 to 6 carbon atoms which is interrupted by a group —NH—, —O—, —CO—, —S—, —SO₂— or —N(R⁵)— in which R⁵ is alkyl having 1 to 4 carbon atoms substituted by sulfo or sulfato, R³ and R⁴ forming with the N atom a heterocyclus, or Y¹ is a group of the formula

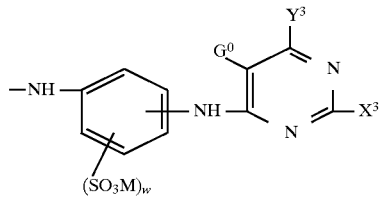

(3A)

in which

M is hydrogen, lithium, sodium or potassium, w is the number zero, 1 or 2 (where, if w is zero, this group is hydrogen), G° is hydrogen, halogen or cyano, X³ is hydrogen, halogen or alkylsulfonyl having 1 to 4 carbon atoms, and Y³ is halogen or methyl;

G is hydrogen, halogen or cyano;

X² is hydrogen, halogen or alkylsulfonyl having 1 to 4 carbon atoms;

Y² is hydrogen, halogen or methyl.

7. An azo compound as claimed in claim 1, in which R¹ is hydrogen, methyl or ethyl.

8. An azo compound as claimed in claim 6, in which X¹ is chlorine or fluorine.

9. An azo compound as claimed in claim 7, in which X¹ is chlorine or fluorine.

10. An azo compound according to claim 6, in which Z is a group of the formula (3a)

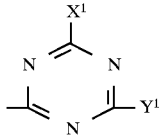

(3a)

in which X¹ is defined as in claim 6 and Y¹ is a group of the formula (4)

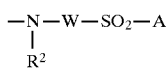 (4)

in which R², W and A are defined as in claim 6.

11. An azo compound as claimed in claim 10, in which $Y^1$ is morpholino.

12. An azo compound as claimed in claim 10, in which $Y^1$ is mono- or disulfophenyl or mono-, di- or trisulfonaphthyl.

13. An azo compound as claimed in claim 6, in which $Y^1$ is morpholino.

14. An azo compound as claimed in claim 6, in which $Y^1$ is mono- or disulfophenyl or mono-, di- or trisulfonaphthyl.

15. An azo compound as claimed in claim 1, in which Z is a group of the formula (8a)

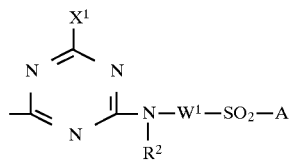 (8a)

in which $X^1$ is chlorine, fluorine or cyanoamino, A is vinyl, or is ethyl which is substituted in the β-position by a substituent which is split off by means of an alkali to form the vinyl group, $R^2$ is hydrogen, ethyl, methyl, β-hydroxyethyl, β-sulfatoethyl, phenyl, 3-sulfo-phenyl or 4-sulfophenyl and $W^1$ is 1,2-ethylene, 1,3-propylene, 2-methyl-1,2-ethylene, 2-methyl-1,3-propylene, 1,4-phenylene, 1,3-phenylene, 2-methoxy-1,5-phenylene, 2,5-dimethoxy-1,4-phenylene, 2-methoxy-5-methyl-1,4-phenylene, 2-sulfo-1,4-phenylene, 2-hydroxy-1,5-phenylene or 2-bromo-1,5-phenylene, where in these groups the 1-position is bonded with the N atom, or 1-sulfonaphth-2,6-ylene, 6-sulfonaphth-2,8-ylene, naphth-2,6-ylene or naphth-2,8-ylene, where in these groups the 2-position is bonded with the N atom.

16. An azo compound as claimed in claim 6, wherein $Y^1$ is a group of the formula (3b)

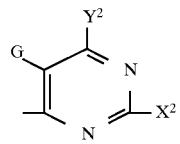 (3b)

in which G, $Y^2$ and $X^2$ have one of the meanings given in claim 6.

17. An azo compound as claimed in claim 1, of the formula (1A)

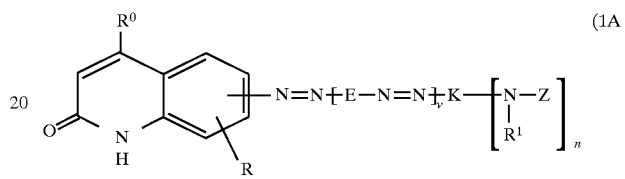 (1A)

in which $R^o$ is hydrogen or methyl, R is hydrogen, methyl, methoxy, chlorine, bromine or sulfo and E, v, K, $R^1$, Z and n have the meanings given in claim 1.

18. An azo compound according to claim 15, wherein A is vinyl, β-chloroethyl or β-sulfatoethyl.

19. An azo compound according to claim 6, wherein A is vinyl, β-chloroethyl or β-sulfatoethyl.

20. An azo compound according to claim 10, wherein A is vinyl, β-chloroethyl or β-sulfatoethyl.

* * * * *